US009642799B2

(12) United States Patent
Broeckx et al.

(10) Patent No.: US 9,642,799 B2
(45) Date of Patent: May 9, 2017

(54) CRYSTALLINE 6-(2-((4-AMINO-3-(3-HYDROXYPHENYL)-1H-PYRAZOLO[3,4-D]PYRIMIDIN-1-YL)METHYL)-3-(2-CHLOROBENZYL)-4-OX0-3,4-DIHYDROQUINAZOLIN-5-YL)-N,N-BIS(2-METHOXYETHYL)HEX-5-YNAMIDE

(71) Applicant: Respivert Limited, Buckinghamshire (GB)

(72) Inventors: Rudy Laurent Maria Broeckx, Beerse (BE); Walter Ferdinand Maria Filliers, Beerse (BE); Patrick Hubert J Nieste, Beerse (BE); Alex Herman Copmans, Beerse (BE); Filip Marcel Vanhoutte, Beerse (BE); Carina Leys, Beerse (BE)

(73) Assignee: Respivert, Ltd., Buckinghamshire (GB)

( * ) Notice: Subject to any disclaimer, the term of this patent is extended or adjusted under 35 U.S.C. 154(b) by 0 days.

(21) Appl. No.: 14/381,289

(22) PCT Filed: Mar. 13, 2013

(86) PCT No.: PCT/GB2013/050624
§ 371 (c)(1),
(2) Date: Aug. 27, 2014

(87) PCT Pub. No.: WO2013/136076
PCT Pub. Date: Sep. 19, 2013

(65) Prior Publication Data
US 2015/0105408 A1  Apr. 16, 2015

Related U.S. Application Data

(60) Provisional application No. 61/610,023, filed on Mar. 13, 2012, provisional application No. 61/610,012, filed on Mar. 13, 2012.

(51) Int. Cl.
| A61K 31/519 | (2006.01) |
| C07D 239/70 | (2006.01) |
| A61K 9/00 | (2006.01) |
| C07D 487/04 | (2006.01) |
| A61K 47/12 | (2006.01) |
| A61K 47/26 | (2006.01) |
| A61K 31/52 | (2006.01) |

(52) U.S. Cl.
CPC .......... *A61K 9/0073* (2013.01); *A61K 9/0075* (2013.01); *A61K 31/519* (2013.01); *A61K 31/52* (2013.01); *A61K 47/12* (2013.01); *A61K 47/26* (2013.01); *C07D 487/04* (2013.01)

(58) Field of Classification Search
CPC ........................... A61K 31/519; C07D 239/70
USPC .............................. 514/262.1; 544/262, 287
See application file for complete search history.

(56) References Cited

U.S. PATENT DOCUMENTS 7,186,401 B2  3/2007  Keller et al.
8,741,909 B2  6/2014  King-Underwood et al.
2006/0239932 A1  10/2006  Monteith et al.
2007/0037805 A1  2/2007  Hayakawa et al.
2011/0135655 A1  6/2011  Katsikis et al.
2012/0082727 A1  4/2012  Cocconi et al.

FOREIGN PATENT DOCUMENTS

| CA | 2347856 | 5/2000 |
| CN | 101448505 A | 6/2009 |
| CN | 201676365 U | 12/2010 |
| CN | 202154919 U | 1/2011 |
| CN | 201692450 U | 3/2012 |
| EP | 1232745 A1 | 8/2002 |
| EP | 1604981 | 12/2005 |
| EP | 1661879 | 5/2006 |
| EP | 1829533 A2 | 9/2007 |
| EP | 1277738 | 3/2011 |
| EP | 2311434 A1 | 4/2011 |
| EP | 1790637 | 1/2014 |
| JP | 2009-513529 A | 4/2009 |
| JP | 2011-153136 A | 8/2011 |
| WO | WO 87/05213 A1 | 9/1987 |
| WO | WO 00/28979 A1 | 5/2000 |
| WO | WO 99/28979 A1 | 5/2000 |
| WO | WO 00/42042 | 7/2000 |
| WO | WO 00/53157 | 9/2000 |
| WO | WO 01/83456 | 11/2001 |
| WO | WO 02/051831 | 7/2002 |
| WO | WO 03/006628 | 1/2003 |
| WO | WO 03/007955 | 1/2003 |
| WO | WO 03/035075 | 5/2003 |
| WO | WO 2004/037176 | 5/2004 |
| WO | WO 2004/080966 | 9/2004 |
| WO | WO 2004/083174 | 9/2004 |
| WO | WO 2004089988 A2 | 10/2004 |
| WO | WO 2005/004845 A1 | 1/2005 |
| WO | WO 2005/007085 | 1/2005 |
| WO | WO 2005/012221 | 2/2005 |
| WO | WO 2005/016348 | 2/2005 |
| WO | WO 2005/016349 | 2/2005 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Rameh, L. E. and Cantley, L. C. "The Role of Phosphoinositide 3-Kinase Lipid Products in Cell Function", *J. Biol. Chem.*, 1999, 274:8347-8350.
Ito, K. et al., "Therapeutic Potential of Phosphatidylinositol 3-Kinase Inhibitors in Inflammatory Respiratory Disease", *J Pharmacol. Exp. Ther.*, 2007, 321:1-8.
Lee, K. S. et al., "Phosphoinositide 3-kinase- δ inhibitor recudes vascular permeability in a murine model of asthma", *J. Allergy Clin. Immunol.*, 2006, 118:403-409.

(Continued)

*Primary Examiner* — Douglas M Willis
(74) *Attorney, Agent, or Firm* — Ada O. Wong

(57) ABSTRACT

There is provided inter alia 6-(2-((4-amino-3-(3-hydroxyphenyl)-1H-pyrazolo[3,4-d]pyrimidin-1-yl) methyl)-3-(2-chlorobenzyl)-4-oxo-3,4-dihydroquinazolin-5-yl)-N,N-bis (2-methoxyethyl)hex-5-ynamide in the form of a solid crystalline hydrate and in solid crystalline anhydrous form. There are also provided dry powder pharmaceutical compositions for inhalation containing such solid crystalline forms.

18 Claims, 19 Drawing Sheets

(56) References Cited

FOREIGN PATENT DOCUMENTS

| | | |
|---|---|---|
| WO | WO 2005/046636 A1 | 5/2005 |
| WO | WO 2005/067901 | 7/2005 |
| WO | WO 2005/112935 | 12/2005 |
| WO | WO 2005/113554 A2 | 12/2005 |
| WO | WO 2005/113556 A1 | 12/2005 |
| WO | WO 2005/117889 | 12/2005 |
| WO | WO 2005/120511 | 12/2005 |
| WO | WO 2006/030925 | 3/2006 |
| WO | WO 2006/089106 | 8/2006 |
| WO | WO 2007/068443 A1 | 6/2007 |
| WO | WO 2007/114926 A2 | 10/2007 |
| WO | WO 2007/134876 A2 | 11/2007 |
| WO | WO 2008/005262 | 1/2008 |
| WO | WO 2008/058402 | 5/2008 |
| WO | WO 2008/058691 A2 | 5/2008 |
| WO | WO 2008/067219 | 6/2008 |
| WO | WO 2008/104077 | 9/2008 |
| WO | WO 2008/127226 A2 | 10/2008 |
| WO | WO 2008/138834 A1 | 11/2008 |
| WO | WO 2008/140750 | 11/2008 |
| WO | WO 2009/088986 | 7/2009 |
| WO | WO 2009/088990 | 7/2009 |
| WO | WO 2010/036380 A1 | 4/2010 |
| WO | WO 2010/059593 | 5/2010 |
| WO | WO 2010/065923 A2 | 6/2010 |
| WO | WO 2010/065932 A1 | 6/2010 |
| WO | WO 2010/111432 | 9/2010 |
| WO | WO 2011/015037 | 2/2011 |
| WO | WO 2011/048111 | 4/2011 |
| WO | WO 2011/083387 A1 | 7/2011 |
| WO | WO 2012/028663 A1 | 3/2012 |
| WO | WO 2012/052753 | 4/2012 |
| WO | WO 2013/136075 A1 | 9/2013 |

OTHER PUBLICATIONS

Lee, K. S. et al.,"Inhibition of phosphoinositide δ attenuates allergic airway inflammation and hyperresponsiveness in murine asthma model", 3-kinase *FASEB J.*, 2006, 20:455-65.
Sadhu, .et al., "Selective role of PI3K δ in neutrophil inflammatory responses", *Biochem. Biophys. Res. Commun.*, 2003, 308:764-9.
Doukas, J. et al., "Aerosolized Phosphoinositide 3-Kinase γ δ Inhibitor TG100-115 {3-{2,4-Diamino-6-(3-hydroxyphenyl)pteridin-7-yl}phenol} as a Therapeutic Candidate for Asthma and Chronic Obstructive Pulmonary Disease" , *J Pharmacol. Exp. Ther.*, 2009, 328:758-765.
To, Y. et al., "Targeting Phosphoinositide-3-Kinase-δ with Theophylline Reserves Corticosteriod Insensitivity in Chronic Obstructive Polmonary Disease", *Am. J. Respir. Crit. Care Med.*, 2010, 182:897-904.
Shah et al, "Evaluation of Two New Tablet Lubricants-Sodium Stearyl Fumarate and Glyceryl Behenate. Measurement of Physical Parameters (Compaction, Ejection and Residual Forces) in the Tableting Process and the Effect on the Dissolution Rate", Drug development and Industrial pharmacy 1986, vol. 12 No. 8-9, pp. 1329-1346.
International Search Report for PCT/GB2013/050624 mailed May 17, 2013.
International Preliminary Report on Patentability for PCT/GB2013/050624 mailed Sep. 25, 2014.
Brittain, H. G., Polymorphism in Pharmaceutical Solids (Second Edition), 2009, vol. 192, ISBN: 9871420031218/1420073214; pp. 1-5; 14-19; 88-95; 120-121; 234-237; 240-241; 318-346; 347-380 and 381-430.
Gautier et al., "Contribution à l'étude des ethers-Oxydes propargyliques", Annales Pharmaceutigues Francaises, 1971, 29, 39-50.
Medicherla, S. et al., "p38α-Selective Mitogen-Activated Protein Kinase Inhibitor Sd-282 Reduces Inflammation in a Subchronic Model of Tobacco smole-Induced Airway Inflammation", J. Pharamcol. Exp. Ther 2008, 342: 921-9.
Khimicheskaya Encyclopedia (Chemical Encyclopedia), vol. 4, pp. 990-993, Sovetskaya Entsiklopediya Moscov, 1988.
Knight et al., Cell, vol. 125, 2006, pp. 733-747.
Aspel et al., Nature Chemical Biology, vol. 4, 2008, pp. 691-699.
Laplante, et al., "Assessing Atropisomer Axial Chemistry Chirality in Drug Discovery and Development", Journal of Medicinal Chemistry, 2011; vol. 54, pp. 7005-7011.
Brana, et al., BMC Medicine, vol. 10: 161, p. 1-15, 2012.
Thomas, et al., Current Opinion in Pharmacology, vol. 8, pp. 267-274, 2008.
Clayden et al., "The Challenge of Atropisomerism in Drug Discovery", Agnew, Chem. Int. Ed. 2009; vol. 48, pp. 6398-6401.
Noriaki Hirayama, "Handbook of Manufacturing Crystals of Organic Compounds", published 2008, pp. 10-11; 57-72 and 78-81, (English Translation of Excerpt).

* cited by examiner

CRYSTALLINE 6-(2-((4-AMINO-3-(3-HYDROXYPHENYL)-1H-PYRAZOLO[3,4-D]PYRIMIDIN-1-YL)METHYL)-3-(2-CHLOROBENZYL)-4-OXO-3,4-DIHYDROQUINAZOLIN-5-YL)-N,N-BIS(2-METHOXYETHYL)HEX-5-YNAMIDE

FIELD OF THE INVENTION

The present invention provides novel crystalline forms of a compound that inhibit phosphoinositide 3-kinases (PI3 kinases), and their use in therapy, especially in the treatment of inflammatory diseases such as COPD and asthma. The novel crystalline forms are suitable for use in dry powder formulations for inhalation.

BACKGROUND OF THE INVENTION

Lipid kinases catalyse the phosphorylation of lipids to produce species involved in the regulation of a wide range of physiological processes, including cellular migration and adhesion. The PI3-kinases are membrane associated proteins and belong to the class of enzymes which catalyse the phosphorylation of lipids which are themselves associated with cell membranes. The PI3-kinase delta isozyme (PI3 kinase δ) is one of four isoforms of type I PI3 kinases responsible for generating various 3'-phosphorylated phosphoinositides, that mediate cellular signalling and has been implicated in inflammation, growth factor signalling, malignant transformation and immunity [See Review by Rameh, L. E. and Cantley, L. C. *J. Biol. Chem.*, 1999, 274:8347-8350].

The involvement of PI3 kinases in controlling inflammation has been confirmed in several models using pan-PI3 kinase inhibitors, such as LY-294002 and wortmannin [Ito, K. et al., *J Pharmacol. Exp. Ther.*, 2007, 321:1-8]. Recent studies have been conducted using either selective PI3 kinase inhibitors or in knock-out mice lacking a specific enzyme isoform. These studies have demonstrated the role of pathways controlled by PI3 kinase enzymes in inflammation. The PI3 kinase δ selective inhibitor IC-87114 was found to inhibit airways hyper-responsiveness, IgE release, pro-inflammatory cytokine expression, inflammatory cell accumulation into the lung and vascular permeability in ovalbumin-sensitized, ovalbumin-challenged mice [Lee, K. S. et al., *J. Allergy Clin. Immunol.*, 2006, 118:403-409 and Lee, K. S. et al., *FASEB J.*, 2006, 20:455-65]. In addition, IC-87114 lowered neutrophil accumulation in the lungs of mice and neutrophil function, stimulated by TNFα[Sadhu, C. et al., *Biochem. Biophys. Res. Commun.*, 2003, 308:764-9]. The PI3 kinase δ isoform is activated by insulin and other growth factors, as well as by G-protein coupled protein signalling and inflammatory cytokines. Recently the PI3 kinase dual δ/γ inhibitor TG100-115 was reported to inhibit pulmonary eosinophilia and interleukin-13 as well as mucin accumulation and airways hyperesponsiveness in a murine model, when administered by aerosolisation. The same authors also reported that the compound was able to inhibit pulmonary neutrophilia elicited by either LPS or cigarette smoke [Doukas, J. et al., *J Pharmacol. Exp. Ther.*, 2009, 328:758-765]

Since it is also activated by oxidative stress, the PI3 kinase δ isoform is likely to be relevant as a target for therapeutic intervention in those diseases where a high level of oxidative stress is implicated. Downstream mediators of the PI3 kinase signal transduction pathway include Akt (a serine/threonine protein kinase) and the mammalian target of rapamycin, the enzyme mTOR. Recent work has suggested that activation of PI3 kinase δ, leading to phosphorylation of Akt, is able to induce a state of corticosteroid resistance in otherwise corticosteroid-sensitive cells [To, Y. et al., *Am. J. Respir. Crit. Care Med.*, 2010, 182:897-904]. These observations have led to the hypothesis that this signalling cascade could be one mechanism responsible for the corticosteroid-insensitivity of inflammation observed in the lungs of patients suffering from COPD, as well as those asthmatics who smoke, thereby subjecting their lungs to increased oxidative stress. Indeed, theophylline, a compound used in the treatment of both COPD and asthma, has been suggested to reverse steroid insensitivity through mechanisms involving interaction with pathways controlled by PI3 kinase δ [To, Y. et al., *Am. J. Respir. Crit. Care Med.*, 2010, 182:897-904].

International patent application WO2011/048111 discloses a number of compounds which are inhibitors of PI3 kinases, particularly PI3 kinase δ, including 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide in the free base form which is disclosed therein as Example 83. This compound is also disclosed in WO2012/052753.

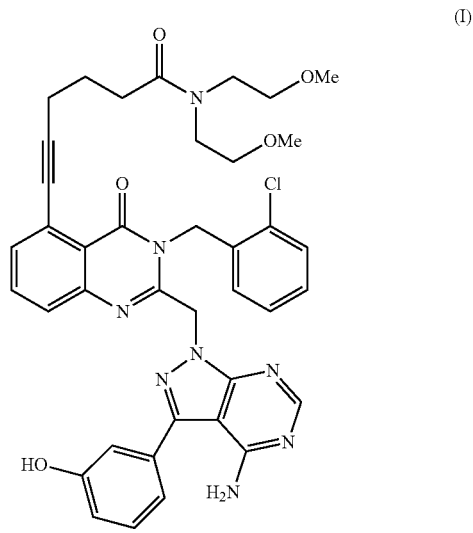 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

(I)

The above mentioned compound is referred to herein as "compound of formula (I)" or "compound of formula (I) free base".

Prior to the applicant'searlier disclosure (WO2011/048111), the PI3 kinase inhibitors described to date have typically been intended for oral administration. However, an undesired consequence of this approach is that non-targeted body tissues, especially the liver and the gut, are likely to be exposed to pharmacologically active concentrations of the drug. An alternative strategy is to design treatment regimens in which the drug is dosed directly to the inflamed organ via topical therapy. In the case of controlling inflammation (or providing another therapeutic effect) in the lungs, this may be achieved by inhalation of the drug, which has the benefit of retaining the drug predominantly in the lungs thereby minimising the risks of systemic toxicity. In order to achieve a sustained duration of action an appropriate formulation which generates a "reservoir" of the active drug may be used.

The compound of formula (I) has, accordingly, been described as being useful for topical administration to the lung (see WO2011/048111).

As well as providing affinity for the target organ and sustained efficacy, a drug for topical administration to the lung via inhalation must also be formulated so as to provide a predictable dose of the drug, which in turn must have predictable and reproducible properties. Achieving acceptable and reproducible chemical and physical stability of the drug in the formulation is a key goal in the product development of pharmaceutical products for all types of pharmaceutical dosage forms. Crystalline forms are preferred, as are forms which are amenable to micronisation.

For inhalation use, there are 3 main dosage forms—a dry powder inhaler (DPI), a metered dose inhaler (MDI) and an aqueous based nebuliser (hand-held or table-top). However the majority of global sales of inhalation products are DPIs and thus provide a well-accepted way of delivering drugs by inhalation. There are numerous commercialized DPI products, such as Flixotide (fluticasone propionate), Advair (fluticasone propionate/salmeterol), Symbicort (budesonide/formoterol), Pulmicort (budesonide), Serevent (salmeterol), Foradil (formoterol).

Dry powder inhalation formulations typically consist of a blend of drug particles (size below 10 microns and normally below 5 microns) with a diluent, typically lactose. Since the usual doses required for inhaled therapies are in the microgram range, the diluent facilitates pharmaceutical processing and dispensing of individual doses e.g. into capsules or blisters or the metering of doses from a bulk reservoir, for subsequent administration to the patient. Therefore, typically, the mass of diluent (the most common being lactose) may be greater than that of the drug substance. In this environment, acceptable formulations of some products can be achieved by simply blending the drug product with lactose. Other products may require other additional excipients or other processing steps in order for the product to meet the requirements of regulatory authorities. For example, U.S. Pat. No. 7,186,401 B2 (Jagotec A G et al.) discloses that the addition of magnesium stearate to dry powder formulations for inhalation improves the moisture resistance of the formulations and allows a high fine particle dosage or fine particle fraction to be maintained under humid conditions. WO00/53157 (Chiesi) describes magnesium stearate as a lubricant to be employed in dry powder formulations for inhalation which is capable if increasing the fine particle dose of certain drugs. US2006/0239932 (Monteith) discloses an inhalable solid pharmaceutical formulation comprising certain active ingredient substances susceptible to chemical interaction with lactose, lactose and magnesium stearate. It is disclosed that magnesium stearate inhibits lactose induced degradation of the active ingredient, presumably via the Maillard reaction which involves the reaction of an amine group on the active ingredient with lactose. US2012/0082727 (Chiesi) discloses a method of inhibiting or reducing chemical degradation of an active ingredient bearing a group susceptible to hydrolysis selected from the group consisting of a carbonate group, a carbamate group and an ester group in a powder formulation for inhalation comprising carrier particles (such as lactose particles) said method comprising coating at least a portion of the surface of said carrier particles with magnesium stearate.

Thus, there remains a need to provide forms of selective PI3 kinase inhibitors for use in inhalation therapy which have the potential to provide therapeutic efficacy in asthma, COPD and other inflammatory diseases of the lungs. In particular, it remains an objective to provide a compound of formula (I) in a crystalline form which has appropriate physical and chemical stability, preferably amenable to micronization, and compatible with pharmaceutical excipients for inhalation therapy, especially lactose.

SUMMARY OF THE INVENTION

In a first aspect, the present invention provides a compound of formula (I)

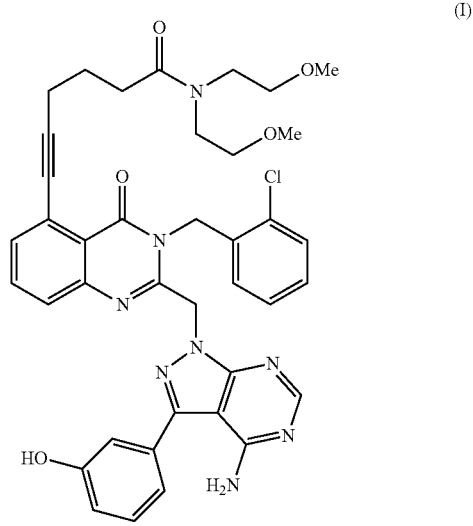 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

(I)

that is 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide in the form of a solid crystalline hydrate.

In a second aspect, the present invention provides a compound of formula (I)

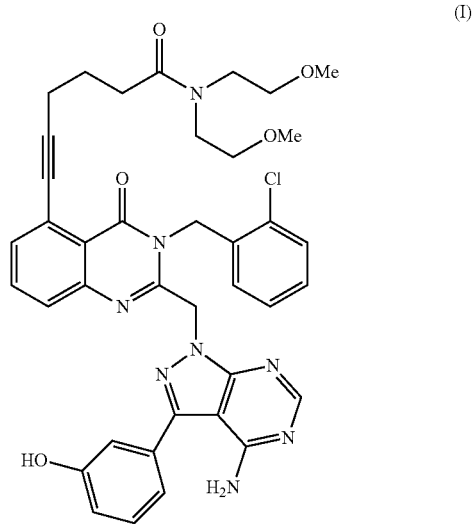 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

(I)

that is 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide in solid crystalline anhydrous form.

Such substances are hereinafter referred to as "solid crystalline forms of the invention". Pharmaceutical formulations which contain the solid crystalline forms of the invention (optionally micronized) are hereinafter referred to as "formulations of the invention".

As explained in the Examples, the solid crystalline forms of the invention have high melting point (around 183° C. or above), appear to have good physical stability (as determined by XRPD, TGA, DSC, DVS and IR analysis) and have good chemical stability (as determined by HPLC analysis). The solid crystalline forms of the invention have good physical stability when combined with lactose. The solid crystalline hydrate form has good chemical stability when combined with lactose. The solid crystalline anhydrous form has good chemical stability when combined with lactose in the presence of a metal salt of stearic acid such as magnesium stearate.

The solid crystalline hydrate form and the solid crystalline anhydrous form appear to have related (but distinct) crystal structures.

DETAILED DESCRIPTION OF THE INVENTION

Figure 1:
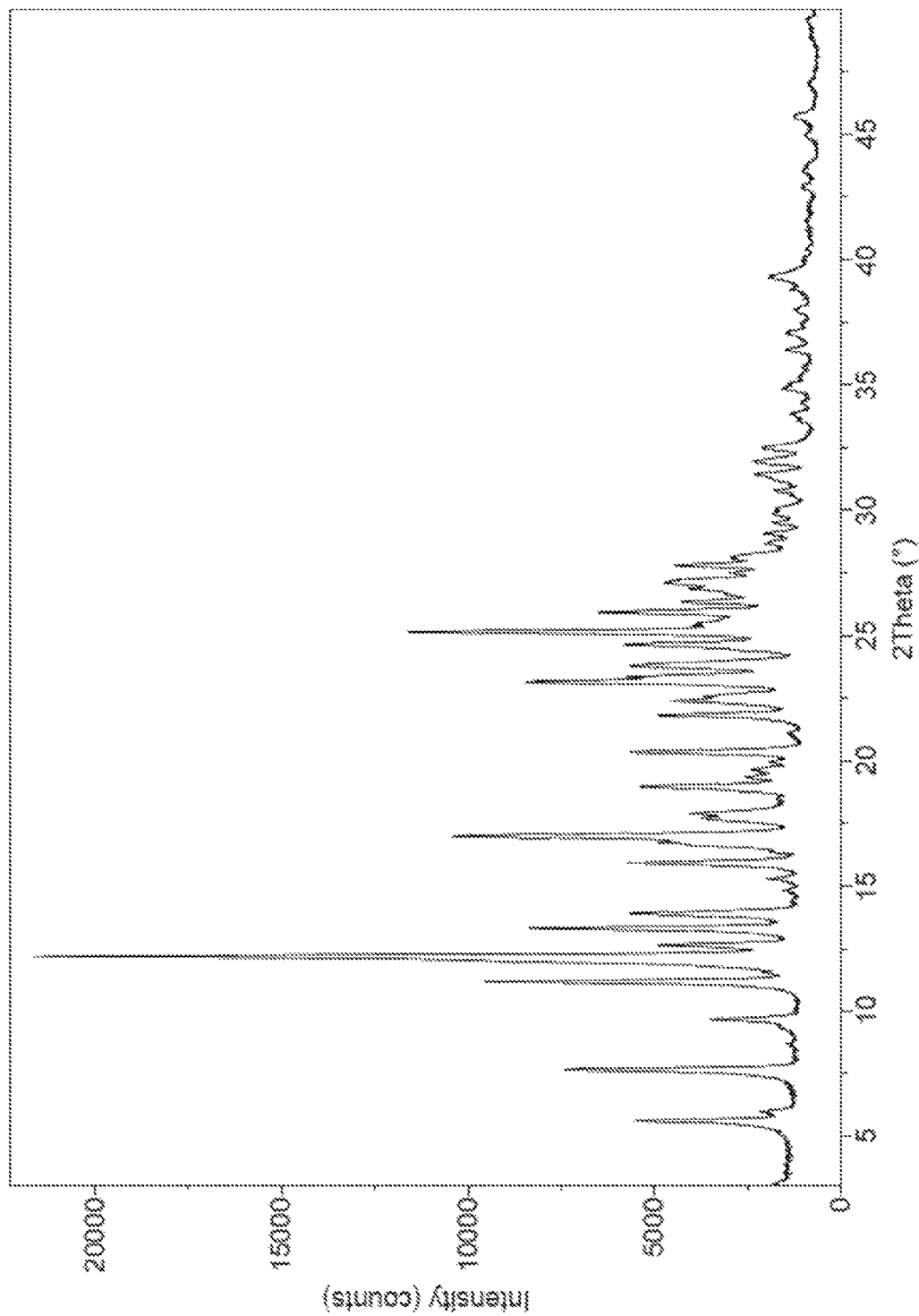
FIG. 1 shows an XRPD pattern acquired on a sample of compound of formula (I) in the form of a solid crystalline hydrate.

Compound of Formula (I) as Active Ingredient

The compound of formula (I) is a dual PI3K delta PI3K gamma inhibitor, wherein the term inhibitor as employed herein is intended to refer to a compound that reduces (for example by at least 50%) or eliminates the biological activity of the target protein, for example the PI3K delta isozyme, in an in vitro enzyme assay. The term delta/gamma inhibitor as employed herein is intended to refer to the fact that the compound inhibits, to some degree, both enzyme isoforms although not necessarily to the same extent. Compound of formula (I) is active in cell based screening systems and thereby demonstrates that it possesses suitable properties for penetrating cells and thereby exert intracellular pharmacological effects.

Generic processes for synthesising the compound of formula (I) are disclosed in WO2011/048111, the contents of which are incorporated by reference in their entirety, and a method similar to that of Example 1 can be employed. See also WO2012/052753, the contents of which are incorporated by reference in their entirety, where a specific method for synthesising the compound of formula (I) is provided in the Example.

Suitably compound of formula (I) is protected from light during and after synthesis e.g. by use of amber glassware or light impervious packaging (e.g. foil packaging).

The pharmaceutical formulation of the invention comprises compound of formula (I) as active ingredient in a therapeutically effective amount. A therapeutically effective amount of compound of formula (I) is defined as an amount sufficient, for a given dose or plurality of divided doses, to achieve a therapeutically meaningful effect in a subject when administered to said subject in a treatment protocol.

Pharmaceutical formulations of the invention are suitably dry powder pharmaceutical formulations for inhalation.

In one embodiment, the dry powder pharmaceutical formulation comprises from about 0.004 wt. % to about 50 wt. % of compound of formula (I) based on weight of the dry powder pharmaceutical formulation and based on weight of compound of formula (I) as free base; for example from about 0.02 wt. % to about 50 wt. %, from about 0.02 wt. % to about 25 wt. %, or from about 0.02 wt. % to about 15 wt. % or from about 0.02 wt. % to about 20 wt. %. Preferably, the dry powder pharmaceutical formulation comprises from about 0.1 wt. % to about 20 wt. % e.g. from about 0.1 wt. % to about 5 wt. % of compound of formula (I) based on the weight of the dry powder pharmaceutical formulation.

A pharmaceutical formulation of the invention may contain compound of formula (I) as a single active ingredient. However, the pharmaceutical formulation may contain further active ingredients. The pharmaceutical formulation may also be co-administered together with one or more other active ingredients (or one or more pharmaceutical formulations containing one or more active ingredients). Exemplary further active ingredients are mentioned below.

Compound of formula (I) is suitably prepared in particulate form such that it is suitable for dry powder inhalation. A pharmaceutical formulation of the invention may typically contain drug particles having a volume median diameter (D50) from about 0.5 µm to about 10 µm particularly from about 1 µm to about 5 µm.

A suitable method for determining particle size is laser diffraction, e.g. using a Mastersizer 2000S instrument from Malvern Instruments. Instruments are also available from Sympatec. For particle size distributions, the median value D50 is the size in microns that splits the particle size distribution with half above and half below. The primary result obtained from laser diffraction is a volume distribution, therefore D50 is actually Dv50 (median for a volume distribution) and as used herein refers to particle size distributions obtained using laser diffraction. D10 and D90 values (when used in the context of laser diffraction, taken to mean Dv10 and Dv90 values) refer to the particle size wherein 10% of the distribution lies below the D10 value, and 90% of the distribution lies below the D90 value, respectively.

Particles of suitable size for use in a dry powder inhalation formulation may be prepared by any suitable method known to the person skilled in the art. Drug particles of suitable size for inhalation may be prepared by particle size reduction methods including milling or more preferably micronization e.g. using a jet mill micronization device (eg as manufactured by Hosokawa Alpine). Alternatively, particulates of suitable size may be produced at the first instance by spray drying, spray freezing, controlled crystallisation approaches e.g. controlled precipitation, super-critical fluid crystallisation, sonocrystallisation or other suitable crystallisation procedure, for example in a continuous crystallisation apparatus. Thus one aspect of the invention provides compound of formula (I) in micronized form.

Solvates—Hydrate Form of Compound of Formula (I)

In one embodiment, there is provided compound of formula (I) in the form of a hydrate. In particular, there is provided compound of formula (I) in the form of a solid crystalline hydrate obtained by crystallizing compound of formula (I) from dichloromethane optionally in mixture with methanol (e.g. containing up to 20% e.g. up to 10% e.g. 4.8% v/v methanol) at ambient temperature e.g. around 22° C. Formation of the hydrate was found not to require the addition of water to the reaction mixture (i.e. any residual water in the solvent, or carried over in product from a previous reaction step and/or moisture in the atmosphere is sufficient). However water may be added to the solvent, e.g. 0.1 to 5% water may be added. The detailed preparation of such a solid crystalline hydrate of compound of formula (I) is provided in Example 1.

In one embodiment, there is provided a solid crystalline hydrate form compound of formula (I) having an XRPD pattern substantially as shown in FIG. 1. The method of obtaining the XRPD data is described in the General Procedures and the data discussed in Example 3.

Thus, there is provided a hydrate form of compound of formula (I) in a crystalline form having an X-ray powder diffraction pattern with at least one (for example, one, two, three, four, five, six, seven, eight, nine, ten, eleven, twelve, thirteen or all fourteen) peaks at 5.6, 7.6, 9.6, 11.1, 12.2, 12.6, 13.3, 13.9, 15.9, 17.0, 18.9, 20.3, 21.8, 23.1 (±0.2 degrees, 2-theta values), these peaks being characteristic of the crystalline hydrate form. The peaks at 9.6, 13.3, 13.9, 17.0, 18.9, 20.3 and 23.1 are particularly characteristic of the hydrate from and therefore it is preferred to see at least one (for example one, two, three, four, five, six or all seven) of these peaks.

Without being limited by theory, the solid crystalline hydrate form of compound of formula (I) may be a channel hydrate form. Alternatively, water may reside in pores in the crystal or at the surface of the crystal. In any event, as shown in the Examples, water does not form an essential part of the crystal lattice and the crystal form is stable to removal or addition of water.

The physical and chemical stabilities of the solid crystalline hydrate form of the compound of formula (I) disclosed herein were investigated.

In order to assess physical stability, samples of the hydrate form of compound of formula (I) were stored in containers open to the ambient atmosphere at different temperatures and relative humidities. The physical stability of the samples was investigated using thermogravimetric analysis (TGA), differential scanning calorimetry (DSC), dynamic vapour sorption (DVS), infrared spectroscopy (IR) and X-ray powder diffraction (XRPD). Full experimental procedures are provided in the General Procedures section and the results are summarized in Example 4 (Table 3). As discussed in Example 4, the hydrate form of compound of formula (I) was found to have good overall physical stability. However, under DVS analysis a weight loss of 2.2% was registered and the obtained dry product was found to be hygroscopic. Small differences in the IR and XRPD data were observed for the samples under drier conditions, however these differences were attributed to the loss of water observed in the DVS studies and the integrity of the crystalline structure was retained after water loss and subsequent rehydration.

In order to assess chemical stability, samples of the hydrate form of compound of formula (I) were prepared in methanol and analysed by HPLC. The results are summarized in Example 5 (Table 6) where it is indicated that the hydrate form of compound of formula (I) was found to be chemically stable, although some sensitivity towards light was detected.

Dry powder pharmaceutical formulations typically comprise lactose as a suitable carrier for the active ingredient. Therefore, the lactose compatibility of the hydrate form of compound of formula (I) was investigated.

Both the physical and chemical compatibilities of the solid crystalline hydrate form of compound of formula (I) with lactose were investigated.

In order to assess physical compatibility, high concentration compositions of the hydrate form of compound of formula (I) and lactose were prepared, then analysed at various temperatures and humidities, as summarized in Example 6. It is evident that the tested mixtures were physically compatible under all investigated conditions.

In order to assess chemical compatibility, lower concentration (relative to those used in the physical compatibility studies) compositions of the hydrate form of compound of formula (I) with lactose were prepared in methanol and analysed by HPLC The results are summarized in Example 7 (Table 9) where it is indicated that the hydrate form of compound of formula (I) and lactose are chemically compatible.

As a result of the inventors' studies, it can be concluded that the hydrate form of compound of formula (I), has good physical and chemically stability. The combination of the hydrate form of compound of formula (I) with lactose has both chemical and physical stability, indicating suitability for use in a pharmaceutical formulation.

Anhydrous Form of Compound of Formula (I)

In one embodiment, there is provided compound of formula (I) in anhydrous form. In particular, there is provided compound of formula (I) in solid crystalline anhydrous form, obtained by crystallizing the hydrate form of compound of formula (I) from 1-propanol. Suitably, the 1-propanol is dry e.g. containing a maximum of around 0.9% w/w water. In one embodiment, the 1-propanol has a maximum of 0.8%, 0.7%, 0.6%, 0.5%, 0.4%, 0.3%, 0.2% or 0.05% w/w of water. Suitably, the 1-propanol has maximum of 0.2% w/w water. Suitably, crystallisation is performed in the presence of a metal scavenger. Suitable metal scavengers are materials that adsorb the metal while being easily separable from the compound of interest (i.e. compound of formula (I)). For example, functionalised silicas are particularly useful as metal scavengers, as once the metal has been adsorbed, the metal-silica complex may then be easily separated from the compound of interest by filtration. Functional groups that form stable complexes with metal ions include groups containing one or more nitrogen and/or sulphur centres, and are well known to the person skilled in the art.

An example of a suitable commercially available metal scavenger is SiliaMetS® Thiol (a thiol-derivatised silica gel suitable for scavenging a variety of metals including Pd, Pt, Cu, Ag and Pb). Suitably, the metal scavenger is present in amount sufficient to ensure that the resulting metal ion concentration is below 20 ppm, preferably below 10 ppm. In one embodiment, the metal scavenger is present at 1-10% w/w, for example 2-8% w/w or 5% w/w based on the weight of the compound of formula (I). Suitably crystallisation is performed by cooling the solution of compound of formula (I) and solvent from elevated temperature, continuously (i.e. continuous cooling) or in stages (i.e. alternating between cooling and holding the solution at a particular temperature). Suitable temperature gradients (continuous or separate) for cooling include 95-15° C., 95-20° C., 90-20° C., 80-20° C. 95-90° C., 95-85° C., 95-80° C. 90-85° C., 80-20° C. In one embodiment, the solution is cooled from 80-95° C. to ambient temperature (e.g. around 20-22° C.). The detailed preparation of such a solid crystalline anhydrous form of compound of formula (I) is provided in Example 2.

Figure 2:
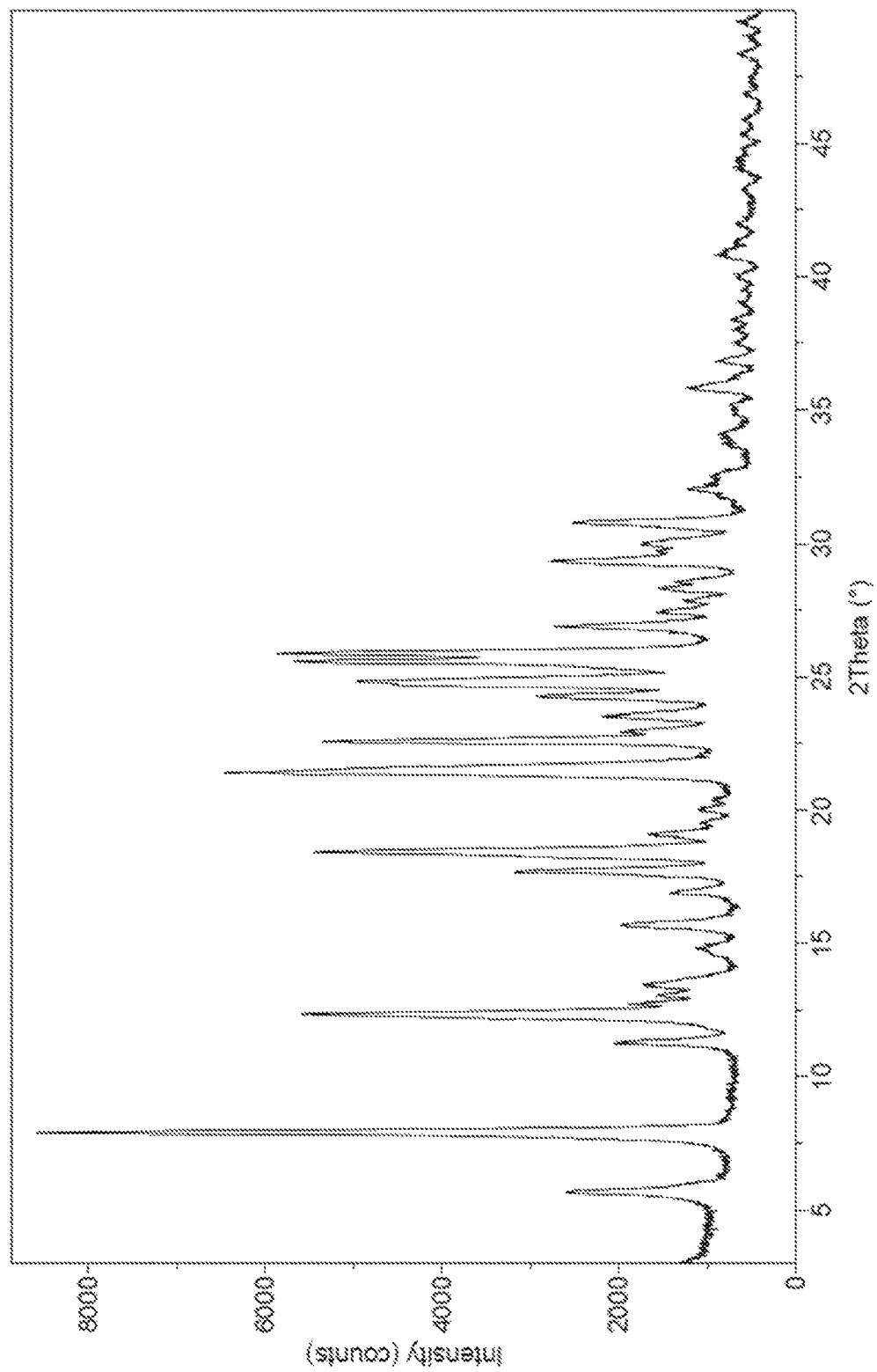
FIG. 2 shows an XRPD pattern acquired on a sample of compound of formula (I) in solid crystalline anhydrous form.

In one embodiment, there is provided a solid crystalline anhydrous form of compound of formula (I) having an X-ray powder diffraction pattern substantially as shown in FIG. 2. The method of obtaining the XRPD data is described in the General Procedures and the data discussed in Example 3.

Thus, there is provided compound of formula (I) in a crystalline anhydrous form having an XRPD pattern with at least one (for example, one, two, three, four, five, six, seven, eight, nine or all ten) peaks at 5.6, 7.9, 11.2, 12.3, 15.6, 17.6, 18.4, 21.4, 22.5, 24.2 (±0.2 degrees, 2-theta values), these peaks being characteristic of the crystalline anhydrous form. The peaks at 17.6, 18.4, 22.5 and 24.2 are particularly characteristic for the anhydrous form and therefore it is preferred to see at least one (for example one, two, three or all four) of these peaks.

The physical and chemical stabilities of the compound of formula (I) in solid crystalline anhydrous form were investigated.

In order to assess physical stability, samples of the anhydrous form of compound of formula (I) in unmicronized and in micronized form were stored in containers open to the ambient atmosphere at different temperatures and relative humidities. Physical stability was investigated using TGA, DSC, DVS, IR and XRPD as described above for the hydrate form of compound of formula (I). The results are summarized in Example 4.

As discussed in Example 4, the anhydrous form of compound of formula (I) (both unmicronized and micronized) was found to be physically stable in all investigated conditions.

In order to assess chemical stability, samples of the anhydrous form of compound of formula (I) (unmicronized and micronized) were prepared in methanol and analysed by HPLC. The results are summarized in Example 5 (Tables 7 and 8) where it is indicated that the anhydrous form of compound of formula (I) (both unmicronized and micronized) was found to be chemically stable, although some sensitivity towards light was detected. It is evident that the chemical stability of the anhydrous form of the compound of formula (I) is comparable with the chemical stability of the hydrate form of compound of formula (I).

The lactose compatibility of the solid crystalline anhydrous form of compound of formula (I) was investigated.

Both the physical and chemical compatibility of the anhydrous form of compound(I) with lactose was investigated.

In order to assess physical compatibility, high concentration compositions of the anhydrous form (micronized) of compound of formula (I) and lactose were prepared, then analysed at various temperatures and humidities, as summarized in Example 6. It is evident that the tested mixtures were physically compatible under all investigated conditions.

In order to assess chemical compatibility, lower concentration (relative to those used in the physical compatibility studies) compositions of the anhydrous form (micronized) of compound of formula (I) with lactose were analysed by HPLC. The results are summarized in Example 7 (Table 10) where it is indicated that under certain conditions the composition of anhydrous form and lactose underwent degradation. The degradation products were investigated and the main degradant was identified by mass spectrometry as being one or both of the two substances shown as D019328:

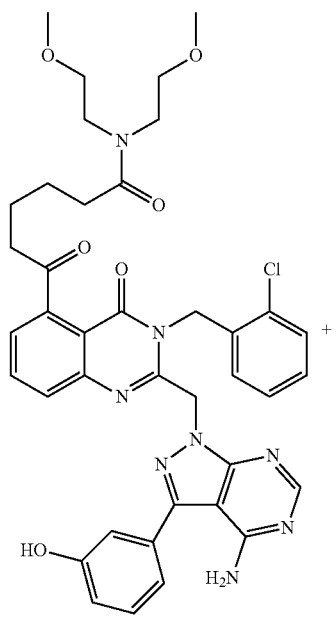

-continued

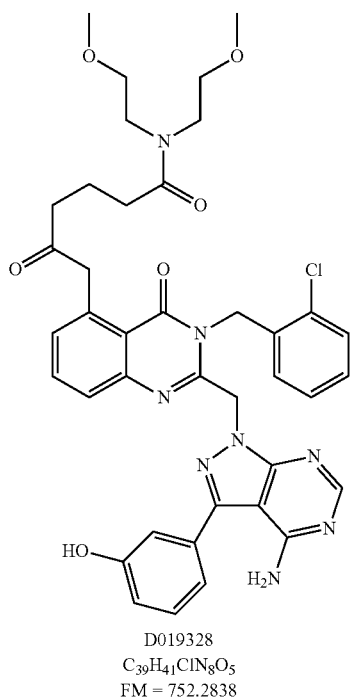

D019328
$C_{39}H_{41}ClN_8O_5$
FM = 752.2838

This degradation product is likely to be the result of the addition of water across the alkyne triple bond and may exist as one of two forms (or may exist in both forms) depending on the orientation of the addition of the water across the triple bond. The same degradant has been observed during the forced degradation of the anhydrous form of compound of formula (I) with metal ions. As a result of further studies, it appears that the degradation of the anhydrous form of compound of formula (I) requires metal ions and water and is accelerated by elevated temperature.

Further investigation involving accelerated stability testing (i.e. exposure of the drug substance to 80° C. in a closed vial, see Example 10) has led the inventors to confirm that at least the degradation product shown as D019492 in Scheme 1 (below) is generated. Moreover the inventors also concluded that a further degradation product (D019493) can result from the hydrolytic cleavage of the pyrimidinone ring and subsequent intramolecular reaction with the alkyne group. D019349 is a presumed intermediary degradation product which was observed in certain circumstances of temperature and RH in stability testing (data not shown).

Scheme 1

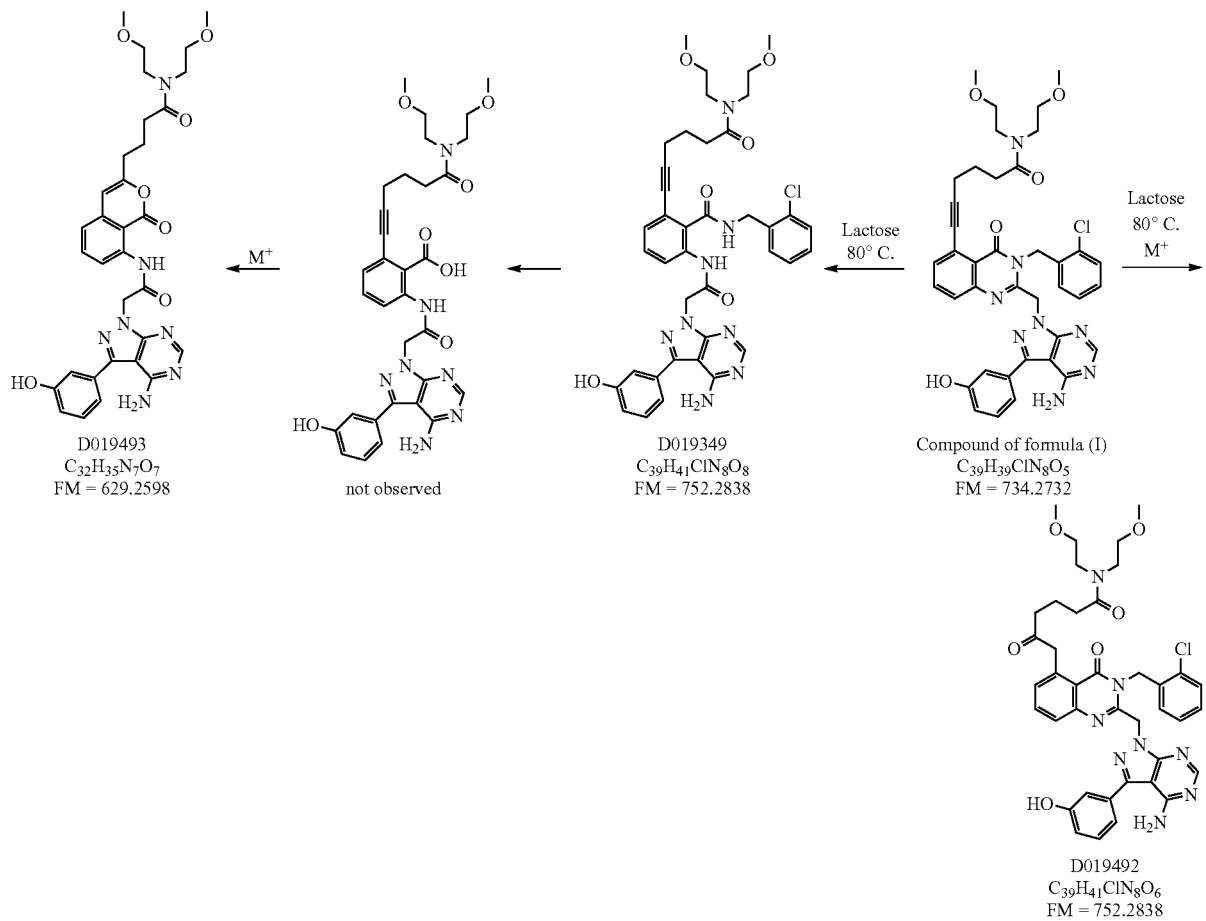

D019493
$C_{32}H_{35}N_7O_7$
FM = 629.2598 not observed

D019349
$C_{39}H_{41}ClN_8O_8$
FM = 752.2838

Compound of formula (I)
$C_{39}H_{39}ClN_8O_5$
FM = 734.2732

D019492
$C_{39}H_{41}ClN_8O_6$
FM = 752.2838

The addition of magnesium stearate to the combination of anhydrous form of compound of formula (I) and lactose was investigated. The combination of anhydrous form of compound of formula (I) with lactose and magnesium stearate was found to be physically stable (Example 8). However, surprisingly, it was found that the addition of magnesium stearate caused an increase in the chemical stability of the combination of anhydrous form of compound of formula (I) and lactose (Example 9). A similar stabilising effect was found using other metal salts of stearic acid, specifically sodium stearate and calcium stearate (Example 10).

Without wishing to be bound by theory, it appears that the metal salt of stearic acid such as magnesium stearate can act as a protecting agent against chemical degradation of the alkyne group in compound of formula (I) and against chemical degradation of the pyrimidinone ring in compound of formula (I) which is observed when the anhydrous form of compound of formula (I) is in a mixture with lactose.

In summary, the inventors have discovered that the solid crystalline anhydrous form of compound of formula (I) has greater physical stability than the solid crystalline hydrate form of compound of formula (I) in isolation, but found that the anhydrous form was less stable with lactose. However, the inventors have discovered that this problem can be overcome by the addition of a metal salt of stearate such as magnesium stearate. The inventors extrapolate these findings with metal salts of stearic acid to metal salts of stearyl fumarate.

Pharmaceutical Formulations for Inhalation

The invention provides pharmaceutical compositions comprising the solid crystalline forms of the invention in admixture with one or more diluents or carriers. Suitably the composition contains lactose as a diluent or carrier.

As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; Frieslandfoods), InhaLac®70 (sieved lactose for dry powder inhaler; Meggle) and Respitose® products. In one embodiment, the lactose component is selected from the group consisting of α-lactose monohydrate, α-lactose anhydrous and amorphous lactose. Preferably, the lactose is α-lactose monohydrate.

In order to penetrate sufficiently far into the lungs, the particulate active ingredient (in this case compound of formula (I)) must be a suitable size as described above. These small particles will have a tendency to agglomerate. The use of a carrier such as lactose prevents this agglomeration and can improve flowability. Furthermore, the use of a carrier ensures that a correct and consistent dosage reaches the lungs. The active ingredient will usually form a monolayer on the larger lactose particle, then during inhalation the active ingredient and the carrier are separated and the active ingredient is inhaled, while the majority of the carrier is not. As such, the use of particulate lactose as a carrier for the active ingredient ensures that each dose of the dry powder pharmaceutical formulation releases the same amount of the active ingredient.

Generally, to prevent agglomeration of the small active particles, a carrier such as lactose with a particle size of approximately or at least ten times that of the active ingredient is used (e.g. lactose having a D50 approximately or at least ten times that of the active ingredient is used).

In one embodiment, the dry powder formulation of the present invention comprises particulate lactose having D50 in the range 40-150 μm.

The dry powder pharmaceutical formulation of the present invention comprises particulate lactose as carrier in an amount sufficient to ensure that the correct and consistent dosage of the active ingredient reaches the lungs. In one embodiment, the dry powder pharmaceutical formulation comprises from about 40 wt. % to about 99.88 or 99.98 wt. %, for example from about 50 wt. % to about 99.88 or 99.98 wt %, from about 65 wt. % to about 99.88 or 99.98 wt. %, or from about 75 wt. % to about 99.88 or 99.98 wt. % of particulate lactose based on the weight of the dry powder pharmaceutical formulation. Preferably, the dry powder pharmaceutical formulation comprises from about 80 wt. % to about 99.98 wt. % or for example from about 80 wt % to about 99.9% wt %, for example from about 85 wt. % to about 99.88 or 99.98 wt. %, for example from about 95 wt. % to about 99 wt. % of particulate lactose based on the weight of the dry powder pharmaceutical composition.

Optionally (and especially when using the solid crystalline anhydrous form) the composition contains a stabilising agent selected from metals salt of stearic acid such as magnesium stearate and metal salts of stearyl fumarate.

An example metal salt of stearic acid is magnesium stearate. Alternative metal salts of stearic acid that may be employed include salts of stearic acid formed with Group I and other Group II metals, such as sodium stearate, calcium stearate and lithium stearate. Other metal salts of stearic acid that may be mentioned include zinc stearate and aluminium stearate.

Metal salts of stearyl fumarate (e.g. sodium stearyl fumarate) appear to have similar properties to those of metal salts of stearic acid (see Shah et al, Drug development and Industrial pharmacy 1986, Vol. 12 No. 8-9, 1329-1346). In the inventors' opinion they can be employed as an alternative to metal salts of stearic acid in the present invention.

As used herein the term "magnesium stearate" includes magnesium stearate trihydrate, magnesium stearate dihydrate, magnesium stearate monohydrate and amorphous magnesium stearate. Magnesium stearate as defined herein includes a tolerance wherein any material defined as "magnesium stearate" may contain up to 25% (e.g. up to 10% e.g. up to 5% e.g. up to 1%) of palmitate salt.

More generally, metal salts of stearic acid or metal salts of stearyl fumarate may be employed in anhydrous form or as a hydrate and may contain up to 25% (e.g. up to 10% e.g. up to 5% e.g. up to 1%) of palmitate salt.

As used herein the expression "stabilizing agent selected from metal salts of stearic acid such as magnesium stearate and metal salts of stearyl fumarate" can include a mixture of metal salts of stearic acid and/or stearyl fumarate, although use of a single salt would be preferred.

The metal salt of stearic acid such as magnesium stearate or metal salt of stearyl fumarate is typically obtained as a fine powder which need not be micronized. Suitably the D50 of the metal salt of stearic acid such as magnesium stearate or metal salt of stearyl fumarate is greater than 5 μm e.g. around 10 μm or greater than 10 μm e.g. in the range 5 to 100 μm e.g. 5 to 50 μm e.g. 5 to 20 μm e.g. 10 to 20 μm. Magnesium stearate may for example be obtained from Avantor (Hyqual 2257 brand) or Peter Greven. Sodium stearate and calcium stearate may, for example, be obtained from Sigma-Aldrich. Sodium stearyl fumarate may, for example, be obtained from ScienceLab.

The dry powder pharmaceutical formulation of the present invention optionally comprises particulate stabilising agent selected from metal salts of stearic acid such as magnesium stearate and metal salts of stearyl fumarate in an amount sufficient to ensure the chemical stability of the formulation ("a stabilising amount"). Chemical stability is, for example, demonstrated when the production of degradant D019328 (one or both substances) is at a level of less than 0.2% wt. % following storage of the composition containing Compound of formula (I) for 4 weeks at 50° C. Alternatively or in addition, chemical stability is, for example, demonstrated when the production of degradant D019493 is at a level of less than 0.5% wt. % following storage of the composition containing Compound of formula (I) for 2 weeks at 80° C. Alternatively, or in addition, chemical stability is, for example, demonstrated when the production of degradant D019492 is at a level of less than 0.4% wt. % following storage of the composition containing Compound of formula (I) for 2 weeks at 80° C. In one embodiment, the dry powder pharmaceutical formulation comprises from about 0.01 wt. % to about 15 wt. %, for example 0.1 wt. % to about 10 wt. %, 10 wt. %, 5 wt. %, 2 wt. % or 1 wt. % of particulate metal salt of stearic acid such as magnesium stearate or metal salt of stearyl fumarate based on the weight of the dry powder pharmaceutical formulation. Preferably, the dry powder pharmaceutical formulation comprises from about 0.5 wt. % to about 5 wt. % e.g. 1-2% w/w of particulate metal salt of stearic acid such as magnesium stearate or metal salt of stearyl fumarate based on the weight of the dry powder pharmaceutical composition. Suitably the metal salt of stearic acid such as magnesium stearate or metal salt of stearyl fumarate is present in an amount sufficient to ensure the physical stability of the formulation. Physical stability is, for example, demonstrated when the IR spectrum and XRPD pattern of the composition (especially in relation to characteristics peaks of Compound of formula (I)) are substantially unaltered following storage of the composition containing Compound of formula (I) for 4 weeks at 50° C.

In one embodiment, the dry powder pharmaceutical formulation for inhalation of the present invention comprises:
(i) From about 0.02 to 50 wt % 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide in solid crystalline anhydrous form in particulate form as active ingredient;
(ii) from about 40 to about 99.88 wt. % particulate lactose; and
(iii) from about 0.1 to about 10 wt. % particulate stabilizing agent selected from metal salts of stearic acid (such as magnesium stearate) and metal salts of stearyl fumarate.

In a further embodiment, the dry powder pharmaceutical formulation for inhalation of the present invention comprises:
(i) From about 0.02 to 50 wt % 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide in the form of a solid crystalline hydrate in particulate form as active ingredient
(ii) from about 40 wt. % to about 99.98 wt. % particulate lactose; and
(iii) optionally from about 0.1 wt. % to about 10 wt. % particulate stabilizing agent selected from metal salts of stearic acid (such as magnesium stearate) and metal salts of stearyl fumarate.

Pharmaceutical Uses and Methods of Administration

There is provided according to one aspect of the present invention use of solid crystalline forms of the invention for use as a medicament.

In one embodiment there is provided the use of a pharmaceutical formulation of the invention for the treatment of COPD and/or asthma, in particular COPD or severe asthma, by inhalation i.e. by topical administration to the lung. Advantageously, administration to the lung allows the beneficial effects of the compounds to be realised whilst minimising the side-effects, for patients.

In one embodiment the pharmaceutical formulation of the invention is suitable for sensitizing patients to treatment with a corticosteroid.

The pharmaceutical formulations may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Topical administration to the lung is achieved by use of an inhalation device.

Thus, an aspect of the invention includes an inhalation device comprising one or more doses of a pharmaceutical formulation according to the invention. Inhalation devices for dry powder formulations are typically breath operated such that the dose is withdrawn from the device and administered to the subject using the power of the subject's lungs by inhaling from a mouthpiece. However, optionally, external energy may be provided to assist the administration of the dose. Typically the inhalation device will comprise a plurality of doses of a pharmaceutical formulation according to the invention, e.g. 2 or 4 or 8 or 28 or 30 or 60 or more doses. Thus the inhalation device may comprise a month's supply of doses. In an embodiment, a dose is metered into a capsule for use one by one in an inhalation device adapted to deliver the contents of a capsule to a subject upon inhalation. Optionally the doses are divided e.g. such that a dose is administered using two (or more) inhalations from the inhalation device. According to one embodiment of the invention the doses of formulation are pre-metered in the inhalation device. For example the pre-metered doses may be contained in the pouches of a blister strip or disk or within capsules. According to another embodiment of the invention the doses are metered in use. Thus the inhalation device contains a reservoir of dry powder and the device meters a dose of powder (typically on a fixed volume basis) prior to or at the time of administration.

Example dry powder inhalation devices include SPINHALER, ECLIPSE, ROTAHALER, HANDIHALER, AEROLISER, CYCLOHALER, BREEZHALER/NEOHALER, FLOWCAPS, TWINCAPS, X-CAPS, TURBOSPIN, ELPENHALER, DISKHALER, TURBUHALER, MIATHALER, TWISTHALER, NOVOLIZER, DISKUS, SKYEHALER, ORIEL dry powder inhaler, MICRODOSE, ACCUHALER, PULVINAL, EASYHALER, ULTRAHALER, TAIFUN, PULMOJET, OMNIHALER, GYROHALER, TAPER, CONIX, XCELOVAIR, PROHALER and CLICKHALER. Another example is MONODOSE inhaler.

Optionally the inhalation device may be over-wrapped for storage to protect against ingress of moisture. A desiccant may optionally be employed within an over-wrap or within the device. Suitably the pharmaceutical formulation according to the invention in the inhalation device is protected from light.

The pharmaceutical formulations according to the invention may also be useful in the treatment of respiratory disorders including COPD, chronic bronchitis, emphysema), asthma, pediatric asthma, cystic fibrosis, sarcoidosis and idiopathic pulmonary fibrosis and especially asthma, chronic bronchitis and COPD.

The pharmaceutical formulations according to the invention may comprise compound of formula (I) as the sole active ingredient, or may comprise additional active ingredients, e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate, flunisolide, ciclesonide, triamcinolone), beta agonists (e.g. terbutaline, bambuterol, salbutamol, levalbuterol, salmeterol, formoterol, clenbuterol, fenoterol, broxaterol, indacaterol, reproterol, procaterol, vilanterol) and/or xanthines (e.g. theophylline), muscarinic antagonists, (e.g. ipratropium, tiotropium, oxitropium, glycopyrronium, glycopyrrolate, aclidinium, trospium), leukotriene antagonists (e.g. zafirlukast, pranlukast, zileuton, montelukast) and/or a p38 MAP kinase inhibitor. It will be understood that any of the aforementioned active ingredients may be employed in the form of a pharmaceutically acceptable salt.

In one embodiment, the pharmaceutical formulation of the invention is administered in combination with an anti-viral agent, for example acyclovir, oseltamivir (Tamiflu®), zanamivir (Relenza®) or interferon.

In one embodiment the combination of compound of formula (I) and other active ingredient(s) are co-formulated in the pharmaceutical formulation of the invention. In another embodiment, the other active ingredient(s) are administered in one or more separate pharmaceutical formulations.

In one embodiment compound of formula (I) is co-formulated in the pharmaceutical formulation of the invention or co-administered in a separate formulation with a corticosteroid, for example for use in maintenance therapy of asthma, COPD or lung cancer including prevention of the latter.

In one embodiment the pharmaceutical formulation of the invention is administered by inhalation and a corticosteroid is administered orally or by inhalation either in combination or separately.

The pharmaceutical formulation of the invention may also re-sensitise the patient's condition to treatment with a corticosteroid, when previously the patient's condition had become refractory to the same.

In one embodiment of the invention a dose of the pharmaceutical formulation employed is equal to that suitable for use as a monotherapy but administered in combination with a corticosteroid. In one embodiment a dose of the pharmaceutical formulation which would be sub-therapeutic as a single agent is employed, and is administered in combination with a corticosteroid, thereby restoring patient responsiveness to the latter, in instances where the patient had previously become refractory to the same.

Additionally, the pharmaceutical formulation of the invention may exhibit anti-viral activity and prove useful in the treatment of viral exacerbations of inflammatory conditions such as asthma and/or COPD.

The pharmaceutical formulation of the present invention may also be useful in the prophylaxis, treatment or amelioration of influenza virus, rhinovirus and/or respiratory syncytial virus.

In one embodiment the presently disclosed pharmaceutical formulations are useful in the treatment or prevention of cancer, in particular lung cancer, especially by topical administration to the lung.

Thus, in a further aspect, the present invention provides a pharmaceutical formulation as described herein for use in the treatment of one or more of the above mentioned conditions.

In a further aspect, the present invention provides a pharmaceutical formulation as described herein for the manufacture of a medicament for the treatment of one or more of the above mentioned conditions.

In a further aspect, the present invention provides a method of treatment of the above mentioned conditions which comprises administering to a subject an effective amount of a pharmaceutical formulation of the invention thereof.

Pharmaceutical formulations described herein may also be used in the manufacture of a medicament for the treatment of one or more of the above-identified diseases.

The word "treatment" is intended to embrace prophylaxis as well as therapeutic treatment.

Unless otherwise specified, % values as used herein are % values by weight (wt. %).

The solid crystalline forms of the invention, and pharmaceutical formulations containing them, may have the advantage that they have improved crystallinity (e.g. as measured by XRPD), improved physical stability (e.g. as measured by XRPD, IR, DVS, DSC or TGA analysis), improved chemical stability (e.g. as measured by HPLC), improved physical compatibility with lactose (optionally when combined with other excipients), improved chemical compatibility with lactose (optionally when combined with other excipients), improved particle size distribution on administration (such as evidenced by improved fine particle mass) or may have other favourable properties as compared with prior art solid forms of the compound of formula (I).

ABBREVIATIONS aq aqueous
COPD chronic obstructive pulmonary disease
d doublet
DCM dichloromethane
DMAP 4-dimethylaminopyridine
DMSO dimethyl sulfoxide
DPI dry powder inhaler
DSC differential scanning calorimetry
DVS dynamic vapour sorption
EDC.HCl 1-ethyl-3-(3-dimethylaminopropyl)carbodiimide hydrochloride
($ES^+$) electrospray ionization, positive mode
EtOAc ethyl acetate
HPLC high performance liquid chromatography
HPLC-MS high performance liquid chromatography mass spectrometry
hr hour(s)
IR infrared
LPS lipopolysaccharide
$(M+H)^+$ protonated molecular ion
MDI metered dose inhaler
MeOH methanol
MEK methylethylketone
MHz megahertz
min minute(s)
mm Millimeter(s)
ms mass spectrometry mTOR mammalian target of rapamycin
m/z mass-to-charge ratio
NH$_4$OAc ammonium acetate
NMR nuclear magnetic resonance (spectroscopy)
Pd(dppf)Cl$_2$ 1,1'-bis(diphenylphosphino)ferrocene]dichloropalladium(II)
ppm parts per million
q quartet
quin quintet
RH relative humidity
RRT relative retention time
R$^t$ retention time
RT room temperature
s singlet
t triplet
TBDMSCl tert-butyldimethylsilyl chloride
TGA thermogravimetric analysis
TNFα tumour necrosis factor alpha
XRPD X-ray powder diffraction

EXAMPLES

General Procedures

HPLC-MS

Performed on Agilent HP1200 systems using Agilent Extend C18 columns, (1.8 μm, 4.6×30 mm) at 40° C. and a flow rate of 2.5-4.5 mL min$^{-1}$, eluting with a H$_2$O-MeCN gradient containing 0.1% v/v formic acid over 4 min. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01-3.50 min, held at 5% H$_2$O-95% MeCN; 3.50-3.60 min, returned to 95% H$_2$O-5% MeCN; flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$. UV detection was performed at 254 nm using an Agilent G1314B variable wavelength detector.

Mass Spectra (MS)

Obtained using electrospray ionization (ESI) over the range m/z 60 to 2000 at a sampling rate of 1.6 sec/cycle using an Agilent G1956B, over m/z 150 to 850 at a sampling rate of 2 Hz using a Waters ZMD or over m/z 100 to 1000 at a sampling rate of 2 Hz using a Shimadzu 2010 LC-MS system.

NMR Spectra $^1$H NMR spectra (except those of Example 10) were acquired on a Bruker Avance III spectrometer at 400 MHz using residual undeuterated solvent as reference.

The $^1$H NMR spectrum for Example 10 was acquired on a Bruker Avance spectrometer at 600 MHz using residual undeuterated solvent as reference.

Dynamic Vapour Sorption (DVS)

Obtained using a Surface Measurement Systems dynamic vapor sorption model DVS-1. Using about 19 mg of the sample, the weight change recorded with respect to the atmospheric humidity at 25° C. was determined using the following parameters:
drying: 60 min. under dry nitrogen
equilibrium: 0.01%/min. for min: 15 min and max: 60 min.
data interval: 0.05% or 2.0 min.
RH (%) measurement points:
first set: 5, 10, 20, 30, 40, 50, 60, 70, 80, 90, 95, 90, 80, 70, 60, 50, 40, 30, 20, 10, 5
second set: 10, 20, 30, 40, 50, 60, 70, 80, 90, 95, 90, 80, 70, 60, 50, 40, 30, 20, 10, 5, 0.

X-Ray Powder Diffraction (XRPD)

XRPD patterns were acquired on a PANalytical (Philips) X'PertPRO MPD diffractometer equipped with a Cu LFF X-ray tube (45 kV; 40 mA; Bragg-Brentano; spinner stage) were acquired using Cu Kα radiation and the following measurement conditions:
scan mode: continuous
scan range: 3 to 50° 2θ
step size: 0.02°/step
counting time: 30 sec/step
spinner revolution time: 1 sec
radiation type: CuKα
Incident Beam Path
program. divergence slit: 15 mm
Soller slit: 0.04 rad
beam mask: 15 mm
anti scatter slit: 1°
beam knife: +
Diffracted Beam Path
long anti scatter shield: +
Soller slit: 0.04 rad
Ni filter: +
detector: X'Celerator
Samples were prepared by spreading on a zero background sample holder.

Infrared Spectrometry (IR)

Micro Attenuated Total Reflectance (microATR) was used and the sample was analyzed using a suitable microATR accessory and the following measurement conditions:
apparatus: Thermo Nexus 670 FTIR spectrometer
number of scans: 32
resolution: 1 cm$^{-1}$
wavelength range: 4000 to 400 cm$^{-1}$
detector: DTGS with KBr windows
beamsplitter: Ge on KBr
micro ATR accessory: Harrick Split Pea with Si crystal Differential Scanning Calorimetry (DSC)

DSC data were collected on a TA-Instruments Q2000 MTDSC equipped with RCS cooling unit. Typically 3 mg of each compound, in a standard aluminium TA-Instrument sample pan, was heated at 10° C./min from 25° C. to 250/300° C. A nitrogen purge at 50 ml/min was maintained over the sample.

Thermogravimetric Analysis (TGA)

TGA data were collected on a TA-Instruments Q500 thermogravimeter Typically 10 mg of each sample was transferred into a pre-weighed aluminium pan and was heated at 20° C./min from ambient temperature to 300° C. or <80[(w/w) %] unless otherwise stated.

Chemical Stability—HPLC

HPLC analysis was carried out using the following operating conditions:

| | |
|---|---|
| Column | Waters Xbridge C18 (150 × 3.0 × 3.5 mm) or equivalent (a column is considered equivalent if performance as specified in SST is met and a comparable separation of all relevant compounds is demonstrated). |
| Column temperature | 35° C. |
| Sample temperature | 10° C. |
| Flow rate | 0.45 ml/min |
| Injection volume | The injection volume can be adjusted as long as the qualification limits of the system are not exceeded (detector and injector) and the peak shape of the main compound is acceptable. As a guide, 30 μl is considered suitable. |
| Detection | UV detection at 255 nm |

Mobile Phase Preparation and Composition:

| A 10 mM ammonium acetate (0.771 g/l) + 0.1%, v/v trifluoroacetic acid in water |
| --- |
| B Acetonitrile |
| Analytical run time is 41 minutes |

| | | Time (minutes) | | | | |
| --- | --- | --- | --- | --- | --- | --- |
| | Solvent | 0 | 35 | 36 | 41 | 42 | 48 |
| Gradient | % A | 95 | 30 | 0 | 0 | 95 | 95 |
| | % B | 5 | 70 | 100 | 100 | 5 | 5 |

With this HPLC method the degradant D019492 elutes at RRT0.86.

Chemical Stability—Ultra High Pressure Liquid Chromatography (UPLC)

UPLC analysis was carried out using the following operating conditions:

| Column | Acquity BEH $C_{18}$; 2.1 × 150 mm; 1.7 μm or equivalent (a column is considered equivalent if performance as specified in SST is met and a comparable separation of all relevant compounds is demonstrated) |
| --- | --- |
| Column temperature | 35° C. |
| Sample temperature | 10° C. |
| Flow rate | 0.40 ml/min |
| Injection volume | The injection volume can be adjusted as long as the qualification limits of the system are not exceeded (detector and injector) and the peak shape of the main compound is acceptable. As a guide, 4 μl is considered suitable. |
| Detection | UV detection at 255 nm |

Mobile Phase Preparation and Composition:

| A 10 mM ammonium acetate (0.771 g/l) + 0.1%, v/v trifluoroacetic acid in water |
| --- |
| B Acetonitrile |
| Analytical run time is 23 minutes |

| | | Time (minutes) | | | | |
| --- | --- | --- | --- | --- | --- | --- |
| | Solvent | 0 | 19 | 20 | 23 | 23.5 | 28 |
| Gradient | % A | 95 | 30 | 0 | 0 | 95 | 95 |
| | % B | 5 | 70 | 100 | 100 | 5 | 5 |

With this UPLC method the degradant D019492 elutes at RRT0.92-0.93 and the degradant D019493 elutes at RRT 0.86-0.87.

Reagents and Suppliers

Lactohale200®: Particle size (Sympatec): D10: 5-15 μm; D50: 50-100 μm; D90: 120-160 μm. Magnesium stearate: Grade Hyqual® 2257; supplied by Avantor. Particle size: D10: typically 3 μm; D50: typically 11.5 μm (10.5-16.5 μm); D90: typically 24 μm (18-28 μm). Supplied as a fine powder

Example 1

Preparation of 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide (Compound of Formula (I)) in the Form of a Solid Crystalline Hydrate 5-Bromo-3-(2-chlorobenzyl)-2-(chloromethyl)quinazolin-4(3H)-one (2)

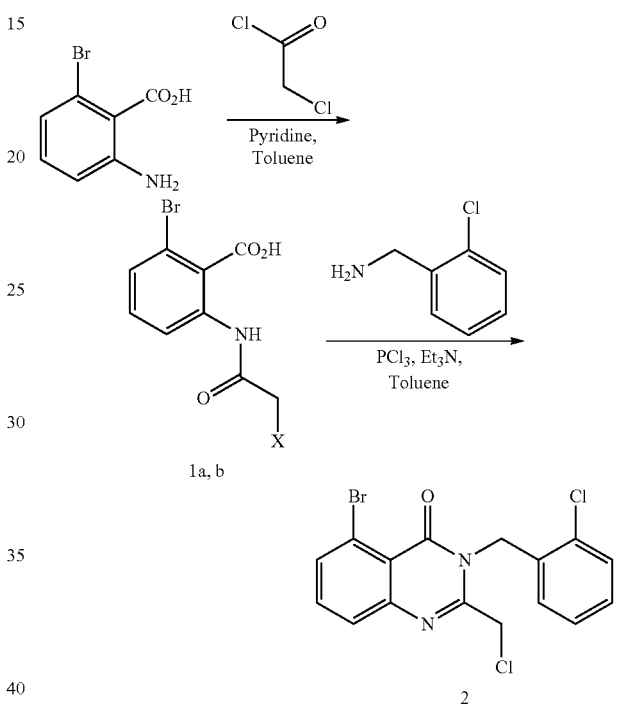

To a stirred solution of 2-amino-6-bromo-benzoic acid (3.06 g, 14.2 mmol) in toluene (75 mL) cooled to 0° C. in an ice-bath was added pyridine (0.60 mL, 7.10 mmol) followed by a solution of chloroacetyl chloride (2.26 mL, 28.4 mmol) in toluene (75 mL) drop-wise over 1 hr. The reaction mixture was allowed to warm to RT, and was heated at 115° C. for 3 hr and then allowed to cool to RT. The solvent volume was reduced by half by evaporation in vacuo. Upon standing overnight, the product precipitated and was collected by filtration to afford 2-bromo-6-(2-chloroacetamido)benzoic acid (1a, X=Cl) (1.44 g) as a white solid: m/z 290/292 (M+H)$^+$ (ES$^+$). The filtrate was concentrated in vacuo and the residue triturated with ethanol/heptane to afford 2-bromo-6-(2-hydroxyacetamido)benzoic acid (1b X=OH) (1.02 g, combined yield, 59%): m/z 274/276 (M+H)$^+$ (ES$^+$). Both 1a and 1b can be used without further purification in the next step.

To a stirred mixture of compound (1a) (7.50 g, 27.4 mmol), 2-chlorobenzylamine (5.00 mL, 41.05 mmol) and triethylamine (5.70 mL, 41.1 mmol) in toluene (250 mL) was added a solution of phosphorus trichloride (2.60 mL, 30.1 mmol) in toluene (250 mL) dropwise over 1 hr. The reaction mixture was heated to 110° C. for 24 hr, whereupon the hot solution was decanted and concentrated in vacuo. The residue was triturated with propan-2-ol (50 mL) to afford the title compound (2) (6.41 g, 59%) as a yellow solid: R$^t$ 2.67 min; m/z 397/399 (M+H)$^+$ (ES$^+$).

3-(3-(tert-Butyldimethylsilyloxy)phenyl)-1H-pyrazolo[3,4-d]pyrimidin-4-amine (6)

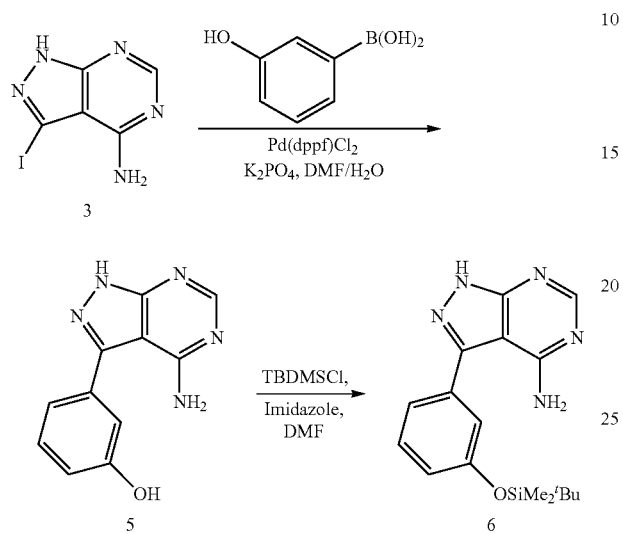

To a stirred suspension of 3-iodo-1H-pyrazolo[3,4-d]pyrimidin-4-amine (3) (8.22 g, 31.5 mmol), 3-phenol boronic acid (13.0 g, 94.5 mmol) and potassium phosphate (10.0 g, 47.3 mmol) in degassed DMF/water (3:2, 140 mL) was added Pd(dppf)Cl$_2$ (13.0 g, 15.7 mmol). The reaction mixture was flushed with nitrogen, heated at 120° C. for 2 hr and then allowed to cool to RT. The reaction mixture was diluted with EtOAc (500 mL) and hydrochloric acid (2 M, 500 mL) and the resulting suspension was filtered. The filtrate was extracted with hydrochloric acid (2 M, 2×500 mL). The combined aqueous extracts were basified with a saturated aqueous solution of sodium carbonate to pH 10. The precipitate formed was filtered and the filtrate was extracted with EtOAc (3×1 L). The combined organic extracts were dried, filtered and the solvent removed in vacuo to afford a grey solid. All solid materials generated during the workup procedure were combined and triturated with DCM to afford 3-(4-amino-1H-pyrazolo[3,4-d]pyrimidin-3-yl)phenol (5) (6.04 g, 84%) as a grey solid: m/z 228 (M+H)$^+$ (ES$^+$).

To a stirred solution of the phenol (5) (4.69 g, 20.66 mmol) and imidazole (2.10 g, 30.99 mmol) in dry DMF (100 mL) was added TBDMSCl (4.70 g, 30.99 mmol). After 16 hr, further aliquots of imidazole (2.10 g, 30.99 mmol) and TBDMSCl (4.70 g, 30.99 mmol) were added and the mixture was stirred for 48 hr. The reaction mixture was diluted with water (120 mL) and extracted with DCM (2×200 mL). The combined organic extracts were washed with water (2×200 mL), dried, filtered and the volume reduced to approximately 100 mL by evaporation in vacuo. The resulting slurry was filtered and the solid washed with heptane (50 mL) to afford the title compound (6) (6.05 g, 85%) as an off-white solid: m/z 343 (M+H)$^+$ (ES$^+$).

Intermediate A 2-((4-Amino-3-(3-hydroxyphenyl)-1H-pyrazolo[3,4-d]pyrimidin-1-yl)methyl)-5-bromo-3-(2-chlorobenzyl)quinazolin-4(3H)-one

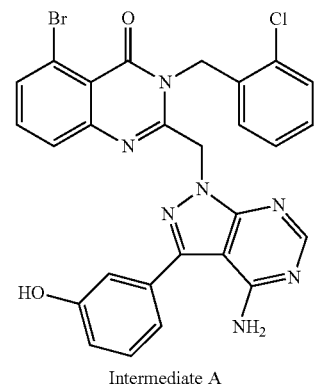

Intermediate A

To a stirred mixture of 5-bromo-3-(2-chlorobenzyl)-2-(chloromethyl)quinazolin-4(3H)-one (2) (100 mg, 0.25 mmol) and potassium carbonate (42 mg, 0.30 mmol) in DMF (2.5 mL) was added a solution of 3-(3-(tert-butyldimethylsilyloxy)phenyl)-1H-pyrazolo[3,4-d]pyrimidin-4-amine (6) (94 mg, 0.28 mmol) in DMF (2.5 mL) and the reaction mixture was stirred at RT for 18 hr. Potassium carbonate (3×35 mg, 0.75 mmol) was added in three portions over 30 hr. after which the solvent was removed in vacuo and the crude material was purified by flash column chromatography, eluting with 4.5% methanol in DCM, to afford the title compound, Intermediate A, (94 mg, 64%) as a off-white solid: R$^t$ 2.01 min; m/z 588/590 (M+H)$^+$, (ES$^+$).

Intermediate B

N,N-bis(2-Methoxyethyl)hex-5-ynamide

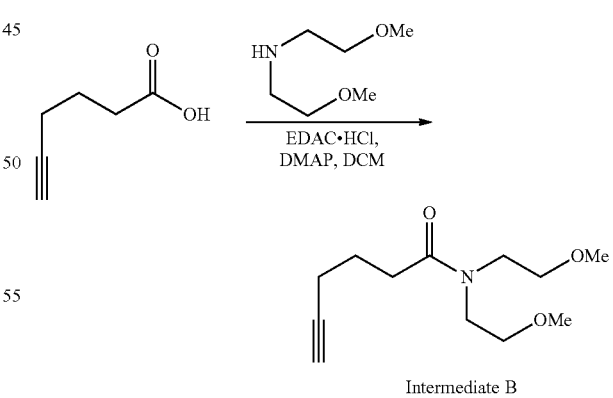

Intermediate B

To a solution of hex-5-ynoic acid (7.11 g, 63.4 mmol), EDC.HCl (14.0 g, 72.9 mmol) and DMAP (387 mg, 3.17 mmol) in DCM (600 mL) at 0° C. was added bis(2-methoxyethyl)amine (9.3 mL, 63 mmol). The resulting mixture was warmed to RT for 20 hr and was then washed with hydrochloric acid (1 M, 2×500 mL) and with water (500 mL). The organic layer was dried and was evaporated in vacuo to afford the title compound, Intermediate B, as a yellow oil (16 g, 97%): $^1$H NMR (400 MHz, CDCl$_3$) δ: 1.88 (3H, m), 2.26 (2H, m), 2.49 (2H, m), 3.32 (6H, s), 3.51 (4H, m), 3.55 (4H, m)

6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide (I)

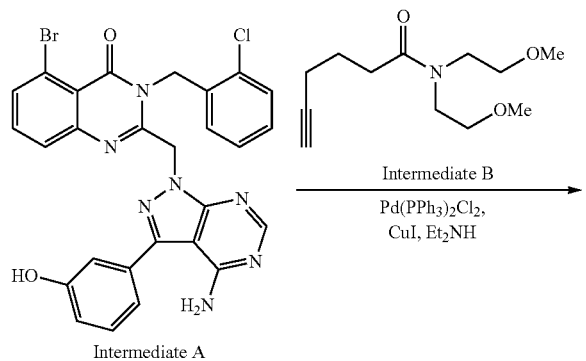

Intermediate A

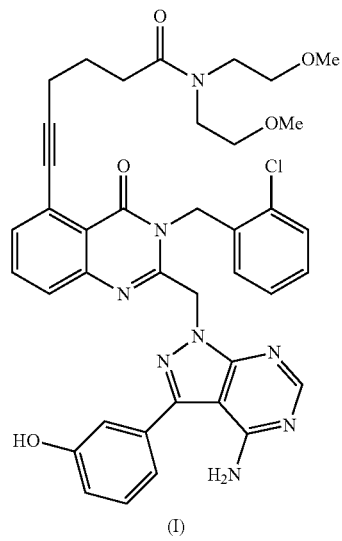

(I)

Intermediate A ((2-((4-amino-3-(3-hydroxyphenyl)-1H-pyrazolo[3,4-d]pyrimidin-1-yl)methyl)-5-bromo-3-(2-chlorobenzyl)quinazolin-4(3H)-one (65.7 g, 1.0 eq.)), copper(I) iodide (1.06 g, 0.05 moles/mol), bis(triphenylphosphine) palladium(II) chloride (3.92 g, 0.05 moles/mol), Intermediate B (N,N-bis(2-methoxyethyl)hex-5-ynamide (63.42 g, 2.5 moles/mol) and diethylamine (837.05 mL; 591.21 g, 7.5 L/mol) were added to a 2 L reactor and the mixture degassed with argon purging. The reaction mixture was warmed to 55° C. (reflux temperature) over 30 minutes and then stirred at 55° C. After 2 hours the mixture was cooled to 22° C. before being concentrated in vacuo to produce a dark brown semi solid residue (201.0 g). The residue was then dissolved in MEK (781 mL) and water added (223 mL). After stirring strongly for 5 minutes the layers were separated and the aqueous layer discarded. The organic layer was washed with 10% w/v aqueous NH$_4$OAc (300 mL) and 2% w/v aqueous NaCl (112 mL) before being partly concentrated in vacuo to an heterogeneous mixture in MEK (230 g). The mixture was stirred for 16 hours then filtered, and the precipitate was washed with MEK (3×25 mL).

The resulting solid was dried at 50° C. in vacuo for 18 hours to give "crude" 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide (compound of formula (I)) (54.13 g; 0.66 equiv; 65.97% yield).

Crude compound of formula (I) (53.5 g; 1.00 equiv), methanol (7.28 mL, 0.1 L/mol) and dichloromethane (145.53 mL, 2 L/mol) were stirred in a 250 mL reactor at 22° C. After 4 hours the solid was filtered and washed with dichloromethane (29 mL) before being dried in vacuo at 40° C. for 18 hours to obtain compound of formula (I) (the title compound) in the form of a hydrate (45.3 g; 0.85 equiv; 84.67% crystallization yield) as an off-white solid.

Example 2

Preparation of Compound of Formula (I) in Solid Crystalline Anhydrous Form

All reactions described within this example were carried out under a flow of nitrogen gas. Compound of formula (I) in the form of a hydrate, as prepared in Example 1 (14.0 g) and 1-propanol (210 mL, 15 L/kg) were added to a 400 ml crystallization vessel. The resulting heterogeneous mixture was stirred and warmed to 90° C. (with the mixture becoming homogeneous at 85° C.). Once the solution had reached 90° C., a metal scavenger (SiliaMetS® Thiol 0.7 g (5% w/w)) was added and the mixture warmed to 95° C. After stirring for 15 minutes at 95° C. the mixture was cooled to 90° C. and stirred for a further 2 hours at 90° C. The metal scavenger was then filtered and the homogeneous filtrate was again stirred and warmed to 95° C., before being cooled to 85° C. and stirred for 8 hours. The filtrate was then cooled over 8 hours to 20° C. and stirred for an additional 6 hours at 20° C. The product was then filtered and washed with 1-propanol (6 ml) before being dried in vacuo at 50° C. for 18 hours to afford compound of formula (I) in anhydrous form (12.6 g, 90%) as a white solid.

The above method may optionally be adapted to facilitate crystallization with seeding.

Example 3

XRPD Analysis of Compound of Formula (I) in Solid Crystalline Hydrate and Anhydrous Form XRPD analysis of the hydrate and anhydrous forms of compound of formula (I) was undertaken using the method described in General Procedures. The resulting diffraction patterns are shown in FIGS. 1 and 2. Both XRPD patterns showed diffraction peaks without the presence of a halo, thereby indicating that both materials are crystalline. Peaks and intensities of the two forms are given below in Tables 1 and 2:

TABLE 1

Characteristic XRPD peaks for compound of formula (I) in a hydrate form
XRPD peak (±0.2 degrees, 2-theta values)

| |
|---|
| 5.6 |
| 7.6 |
| 9.6 |
| 11.1 |
| 12.2 |
| 12.6 |
| 13.3 |
| 13.9 |
| 15.9 |
| 17.0 |
| 18.9 |
| 20.3 |
| 21.8 |
| 23.1 |

TABLE 2

Characteristic XRPD peaks for the anhydrous form of compound (I)
XRPD peak (±0.2 degrees, 2-theta values)

| |
|---|
| 5.6 |
| 7.9 |
| 11.2 |
| 12.3 |
| 15.6 |
| 17.6 |
| 18.4 |
| 21.4 |
| 22.5 |
| 24.2 |

The two solid crystalline forms have some peaks in common indicating that they appear to have related (but distinct) crystal structures.

Example 4

Thermal Analysis of Compound of Formula (I) in Hydrate and Anhydrous Form (Anhydrous Form with and without Micronization)

Thermal analysis of the hydrate form and anhydrous form (anhydrous form unmicronized and micronized) of compound of formula (I) was undertaken using TGA, DVS, XRPD, IR and DSC as described in General Procedures. Where appropriate, a sample at ambient temperature and relative humidity (reference sample/"0 days") was compared with samples stored at various temperatures and relative humidities (comparative samples).

Micronized anhydrous form of compound of formula (I) was prepared using a jet mill micronization device (1.5 bar) (manufactured by Hosokawa Alpine). The Particle Size Distribution was measured using laser diffraction (Malvern Mastersizer instrument). Micronized anhydrous form of compound of formula (I) had the following particle size distribution: D10 of 1.40 μm; D50 of 2.77 μm and D90 of 5.29 μm.

The tested storage conditions were 4 weeks at RT<5% RH, RT 56% RH, RT 75% RH, 50° C. and 40° C. 75% RH. XRPD and IR data were also acquired after 1 week at 80° C.

Solid Crystalline Hydrate Form

Figure 11:
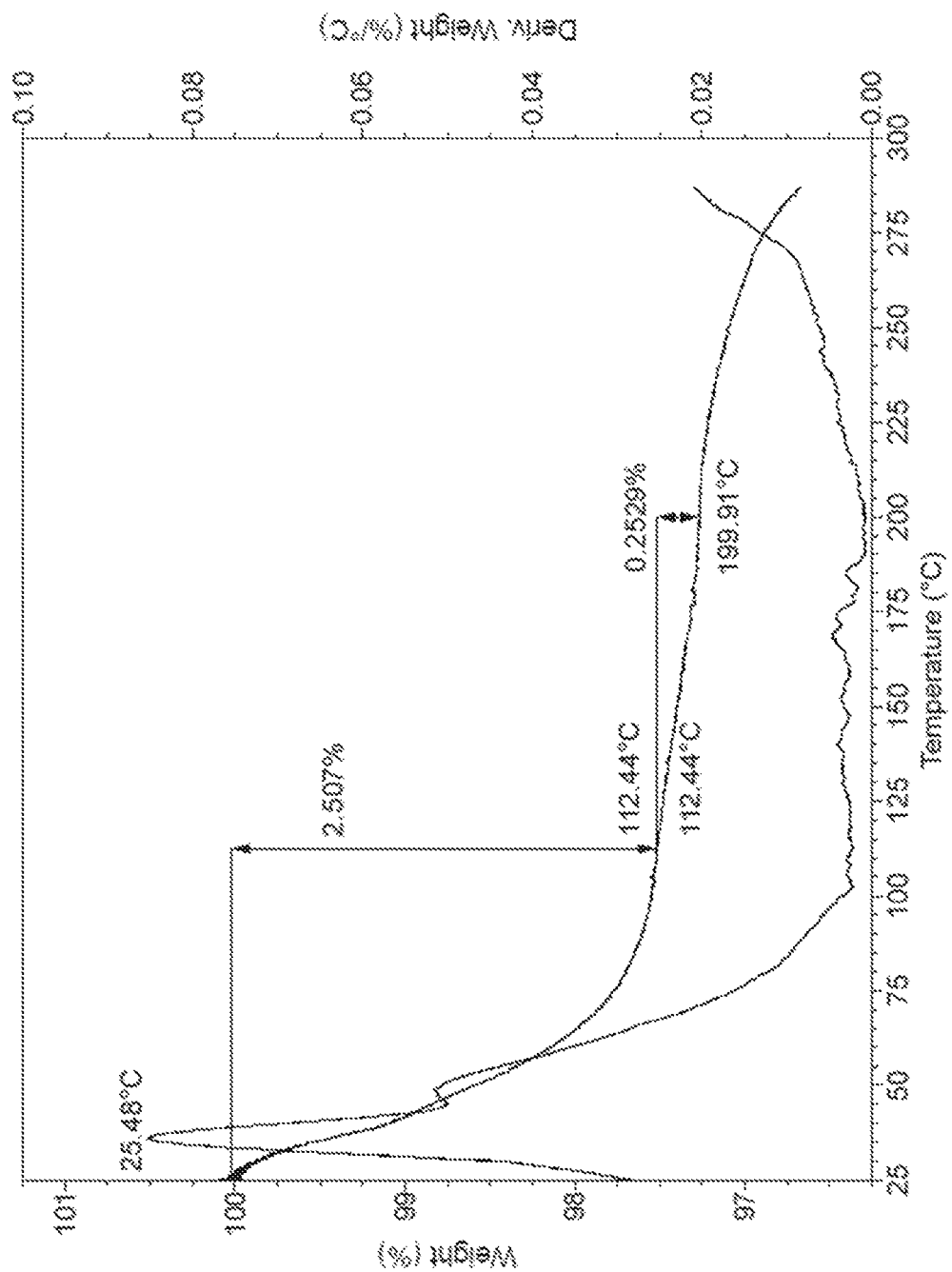
FIG. 11 shows thermal analysis of a sample of compound of formula (I) in the form of a solid crystalline hydrate by TGA.

TGA:

The reference sample (t=0) and comparative samples (exposed to different storage conditions) were heated at 20° C./min from RT to 300° C. The TGA curve of the reference sample (t=0) is illustrated in FIG. 11 and the results for all samples are illustrated in Table 3. From FIG. 11 it is evident weight loss of 1.1% was observed in the temperature region from RT up to 45° C. due to the evaporation of free solvent or hygroscopic water (as evidenced by the first peak between 29.39° C. and 44.82° C.). Weight loss of 1.5% was observed between 45° C. and 190° C. due to the evaporation of bound solvent, and weight loss above 190° C. was due to evaporation and decomposition of the product. Comparing this weight loss profile with those of the comparative samples in Table 3, no significant differences were observed.

Figure 3:
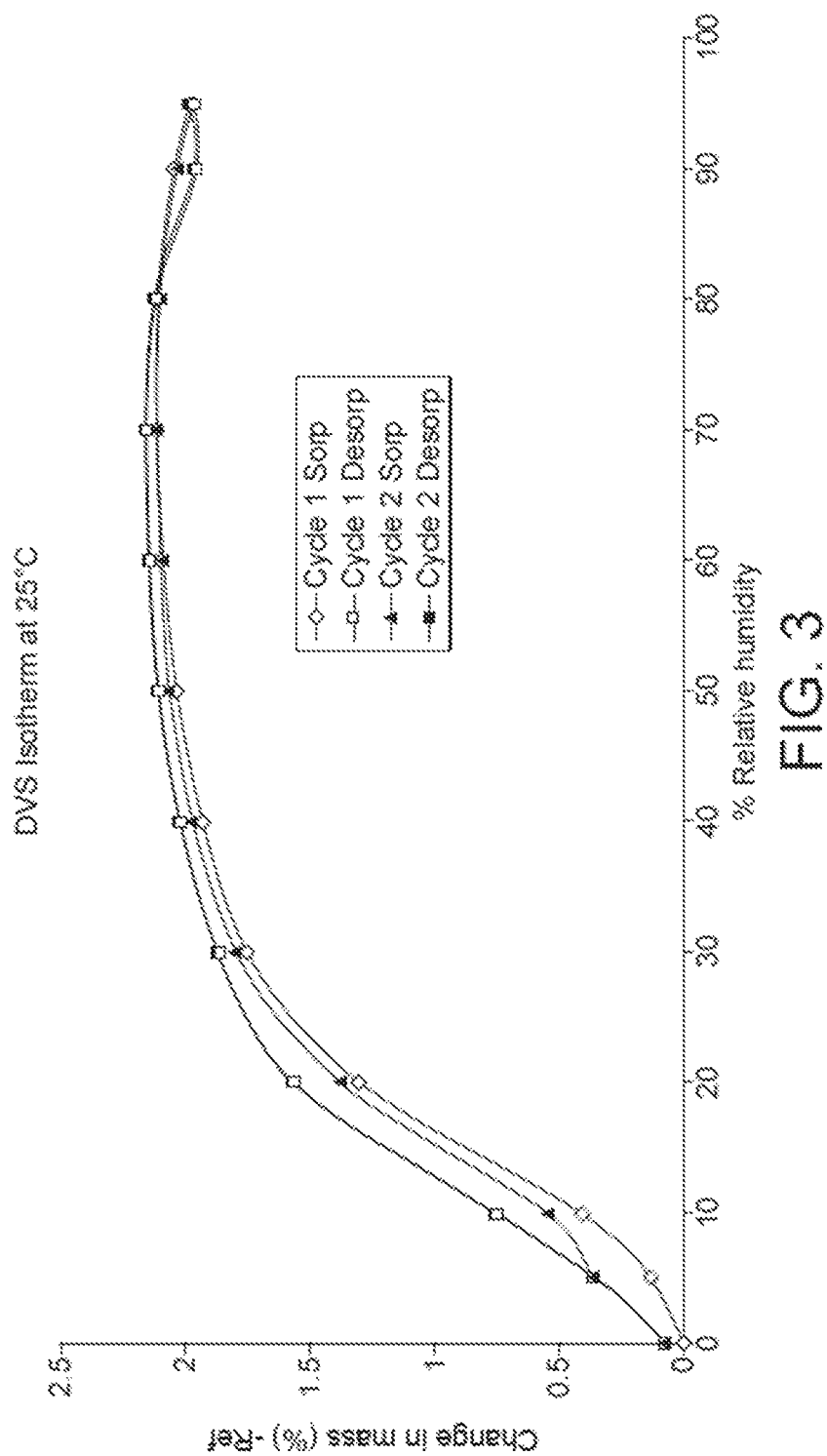
FIG. 3 shows a DVS isotherm plot of a sample of compound of formula (I) in the form of a solid crystalline hydrate.
Figure 4:
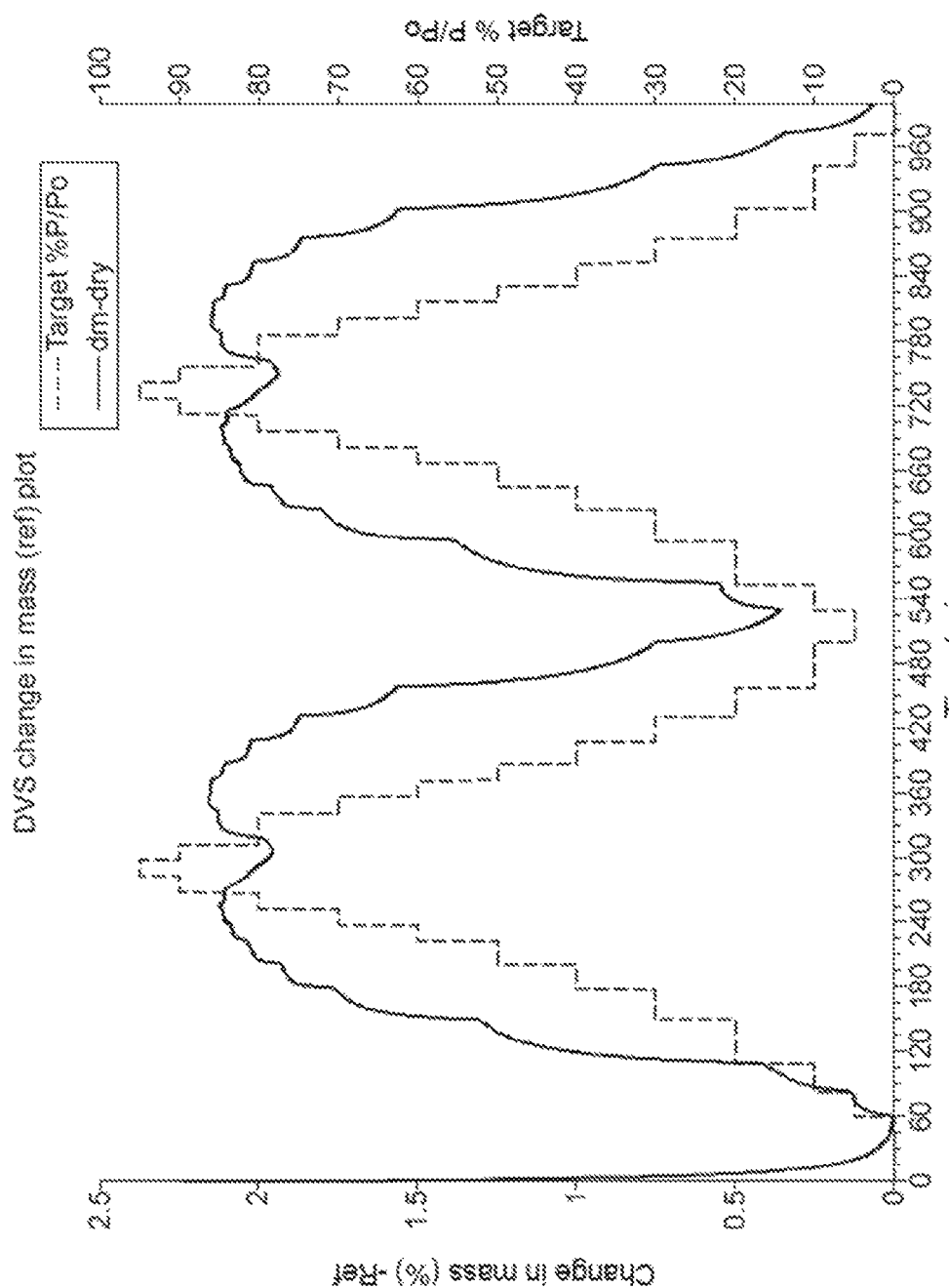
FIG. 4 shows a DVS change in mass plot of a sample of compound of formula (I) in the form of a solid crystalline hydrate.

DVS:

The DVS isotherm plot for the reference sample is illustrated in FIG. 3 and the DVS change in mass plot is illustrated in FIG. 4. During the initial drying step, a weight loss of 2.2% was registered and the obtained dried product was found to be hygroscopic. The hygroscopic product adsorbed up to 2.1% moisture depending on the atmospheric humidity and dried completely during the desorption cycle. The obtained product after adsorption/desorption was investigated with XRPD and IR and was found to be comparable to the reference sample. These data indicate that the hydrate form is hygroscopic.

Figure 7:
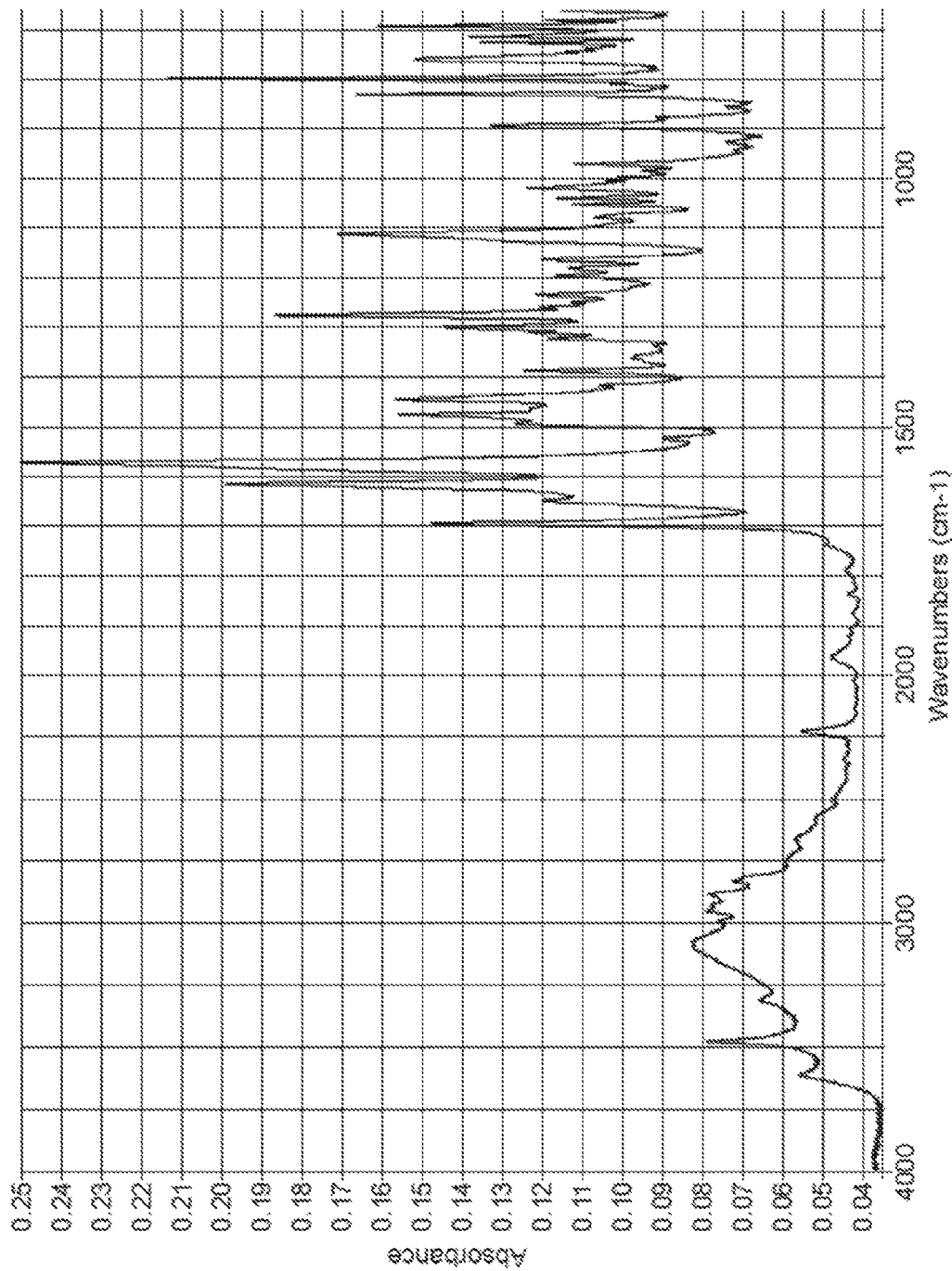
FIG. 7 shows an IR spectrum of a sample of compound of formula (I) in the form of a solid crystalline hydrate.

XRPD and IR:

The XPRD diffraction pattern of the reference sample (t=0) is illustrated in FIG. 1 and the IR trace is illustrated in FIG. 7. This diffraction pattern and IR trace were compared with those of the comparative samples (exposed to different storage conditions) and the results are illustrated in Table 3. The diffraction patterns and IR traces were identical or very similar for most samples, however some small differences in the XRPD diffraction patterns and IR traces were observed after storage at elevated temperatures of 50° C. and 80° C. and under dry conditions (RT/<5% RH), when compared with the reference sample (as evidenced by the "±Ref" entries in Table 3). These same small differences were also observed in the XRPD pattern and IR trace of the reference sample after DVS, suggesting that the differences observed in the 50° C., 80° C. and RT<5% RH samples were due to drying of the product.

Figure 9:
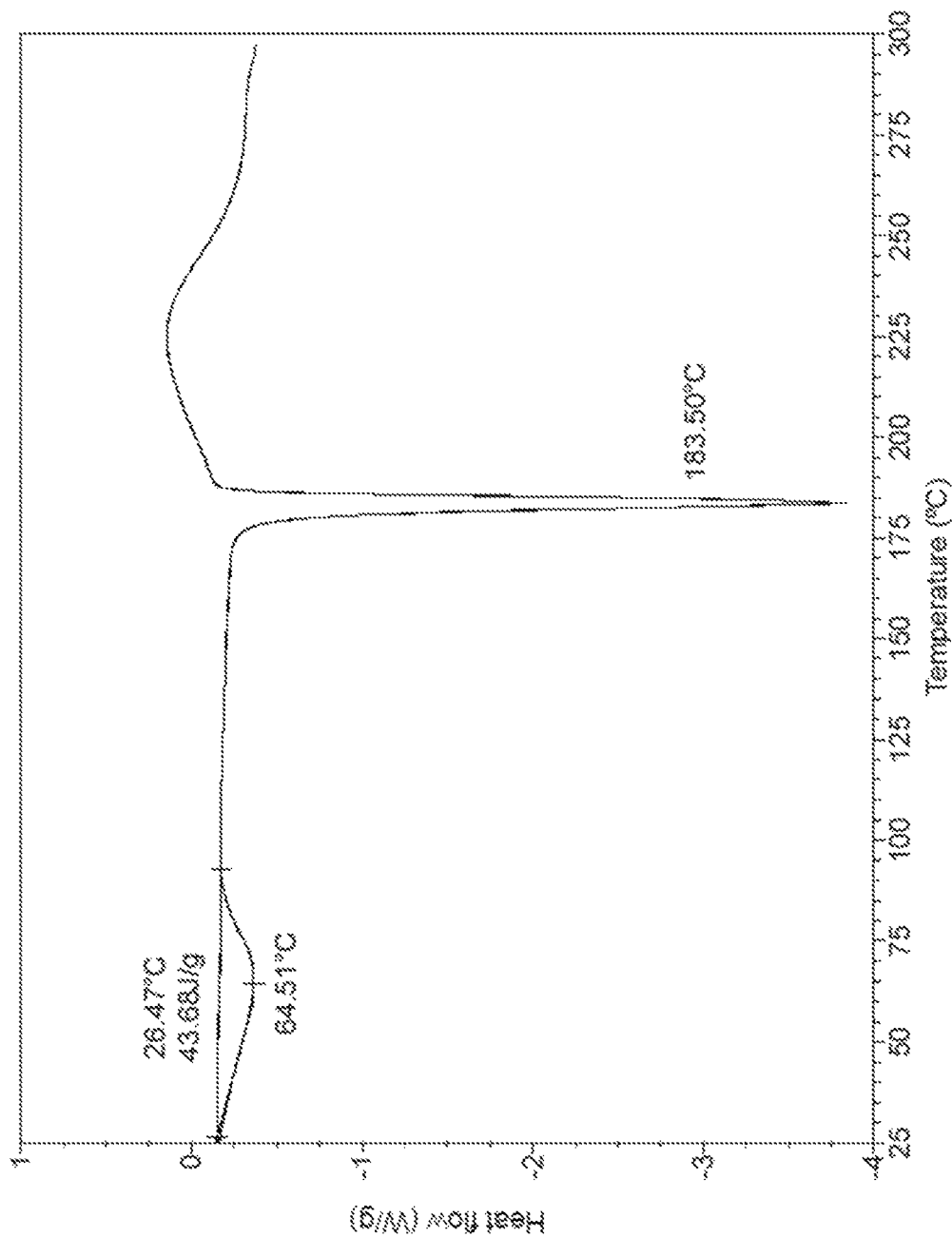
FIG. 9 shows thermal analysis of a sample of compound of formula (I) in the form of a solid crystalline hydrate by DSC.

DSC:

The reference sample (t=0) and comparative samples (exposed to different storage conditions) were heated at 10° C./min from 25° C. to 300° C. The DSC curve of the reference sample is illustrated in FIG. 9 and the results for all samples are illustrated in Table 3. From FIG. 9, it is evident that the reference sample melted with decomposition at about 183.5° C. with an endothermic signal at 64.5° C. due to solvent evaporation.

In summary, it is evident that the hydrate has good physical stability. The product appears to be hygroscopic and experiences some loss of water under dry conditions. However the crystalline form appears to be stable to water loss and water gain.

TABLE 3 stability data for the hydrate form of the compound of formula (I)

| Product | Condition | TGA <45° C. | TGA <190° C. | XRD | IR | DSC Max (° C.) | DSC Extra (° C.) | Appearance |
|---|---|---|---|---|---|---|---|---|
| Hydrate | 0 days* | 1.1 | 1.5 | Cryst., Ref | Cryst, Ref | 183.5 | 64.5 (44 J/g) | white |
| | RT/<5% RH | 0.7 | 0.9 | ±Ref | ±Ref | 183.6 | 62.7 (23 J/g) | white |
| | RT/56% RH | 1.0 | 1.1 | ~Ref | ~Ref | 183.5 | 66.0 (40 J/g) | white |
| | RT/75% RH | 1.2 | 1.3 | ~Ref | ~Ref | 183.5 | 65.3 (40 J/g) | white |
| | 80° C. (1 week) | — | — | ±Ref | ±Ref | — | | white |
| | 50° C. | 1.0 | 1.0 | ±Ref | ±Ref | 183.7 | 64.7 (37 J/g) | white |
| | 40° C./75% RH | 0.9 | 1.0 | ~Ref | ~Ref | 183.4 | 66.9 (39 J/g) | white |

Figure 12:
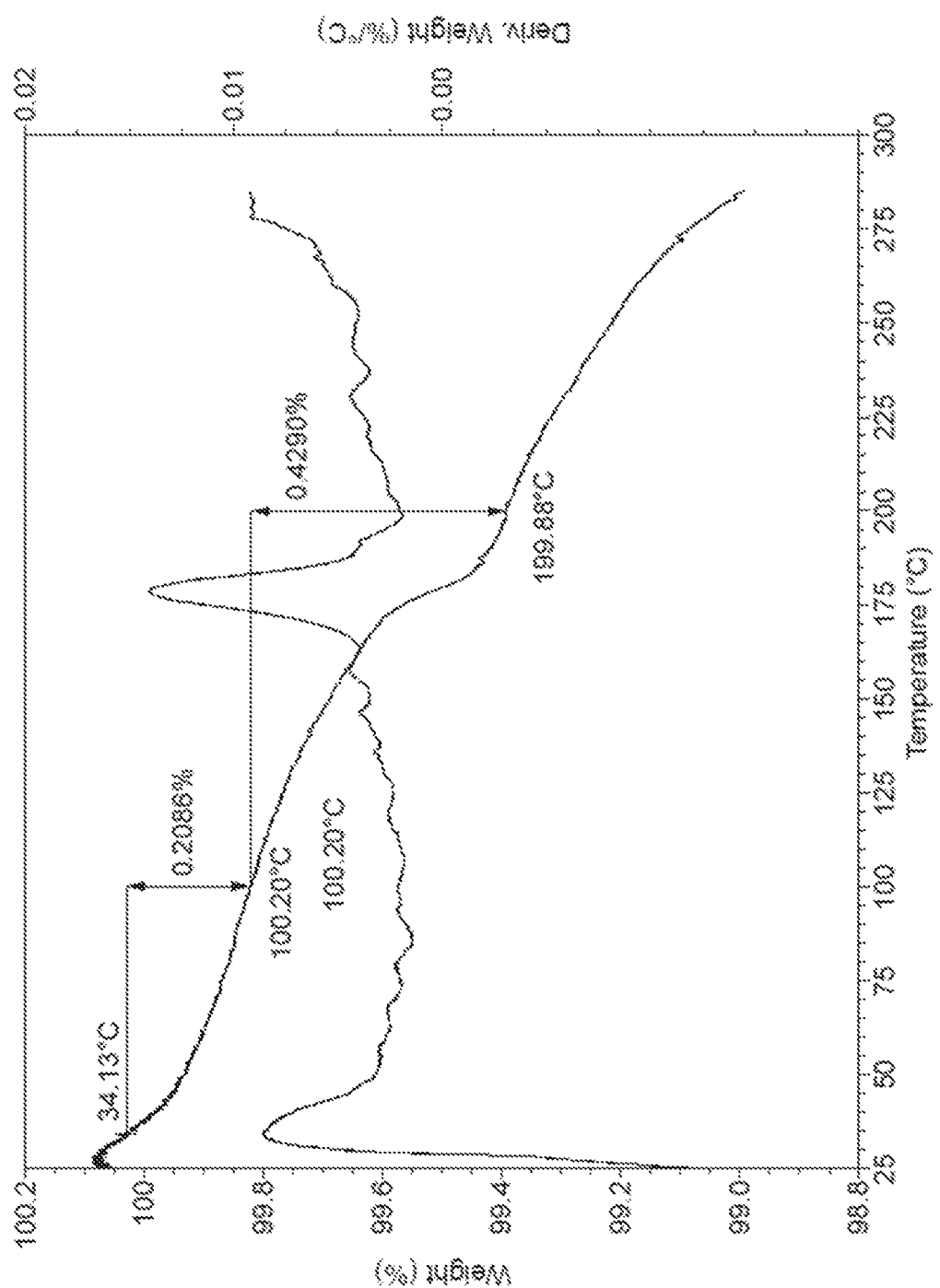
FIG. 12 shows thermal analysis of a sample of compound of formula (I) in solid crystalline anhydrous form by TGA.

*ambient temperature and relative humidity
Cryst., Ref: crystalline reference
~Ref: identical to crystalline reference
+/−Ref: comparable to crystalline reference Solid Crystalline Anhydrous Form (not Micronized)
TGA (Table 4 and FIG. 12): The reference sample and comparative samples were heated at 20° C./min from room temperature to 300° C. The TGA curve of the reference sample (t=0) is illustrated in FIG. 12 and the results for all samples are illustrated in Table 4. From FIG. 12 it is evident that for the reference sample weight loss of 0.2% was observed in the temperature region from room temperature up to 100° C. due to the evaporation of free solvent and/or hygroscopic water. Weight loss of 0.4% was observed between 100° C. and 200° C., probably due to the evaporation and decomposition of the product. Comparing this weight loss profile with those of the comparative samples—differences were observed under dry conditions of RT/<5% RH where lower % weight losses of 0.7% and 0.9% occurred.

Figure 5:
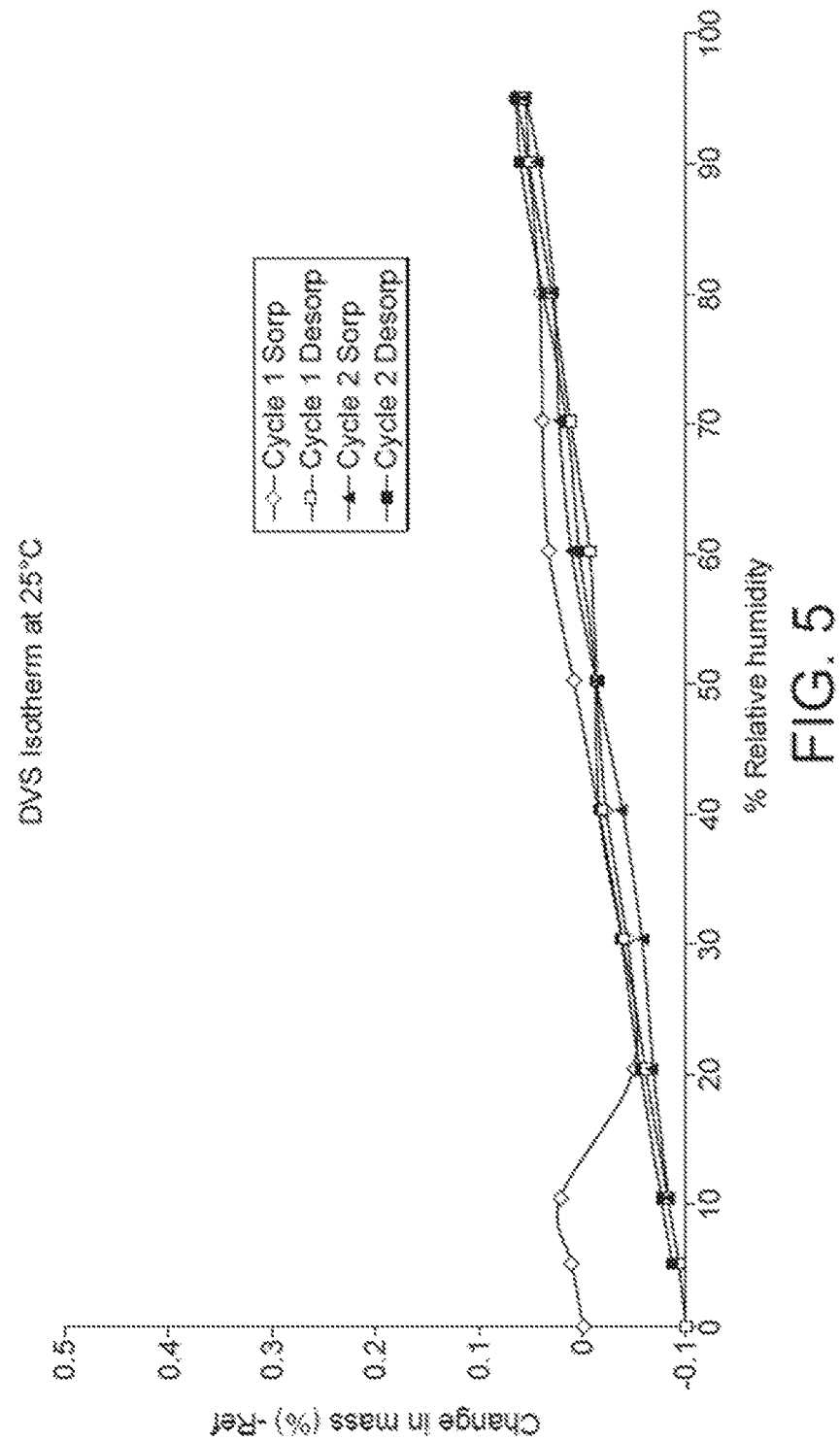
FIG. 5 shows a DVS isotherm plot of a sample of compound of formula (I) in solid crystalline anhydrous form.
Figure 6:
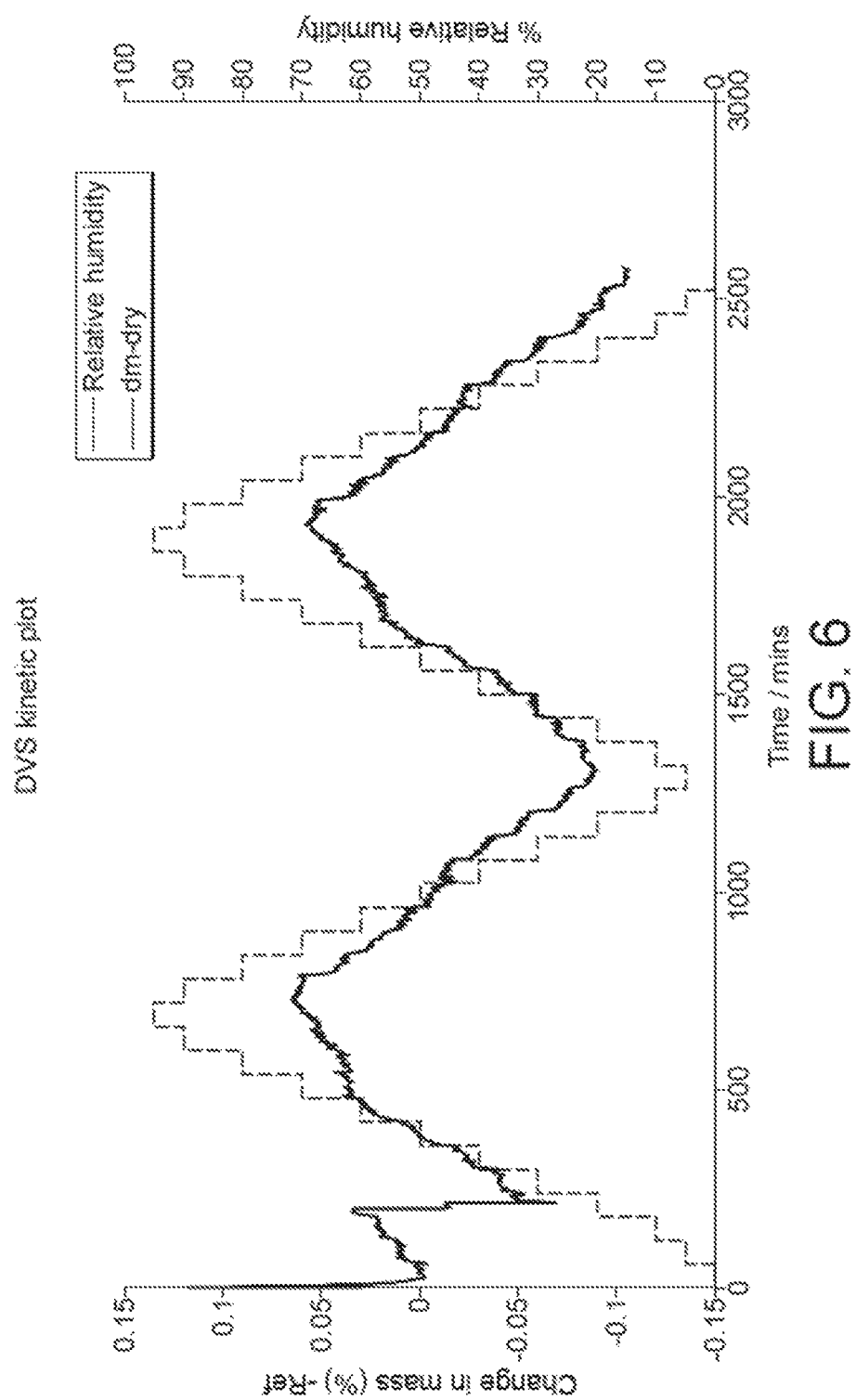
FIG. 6 shows a DVS change in mass plot of a sample of compound of formula (I) in solid crystalline anhydrous form.

DVS:

The DVS isotherm plot for the reference sample is illustrated in FIG. 5 and the DVS change in mass plot is illustrated in FIG. 6. During the initial drying step, a weight loss of 0.1% was registered. The obtained dried product exhibited no hygroscopic behavior and remained in the same solid state form during the test.

Figure 8:
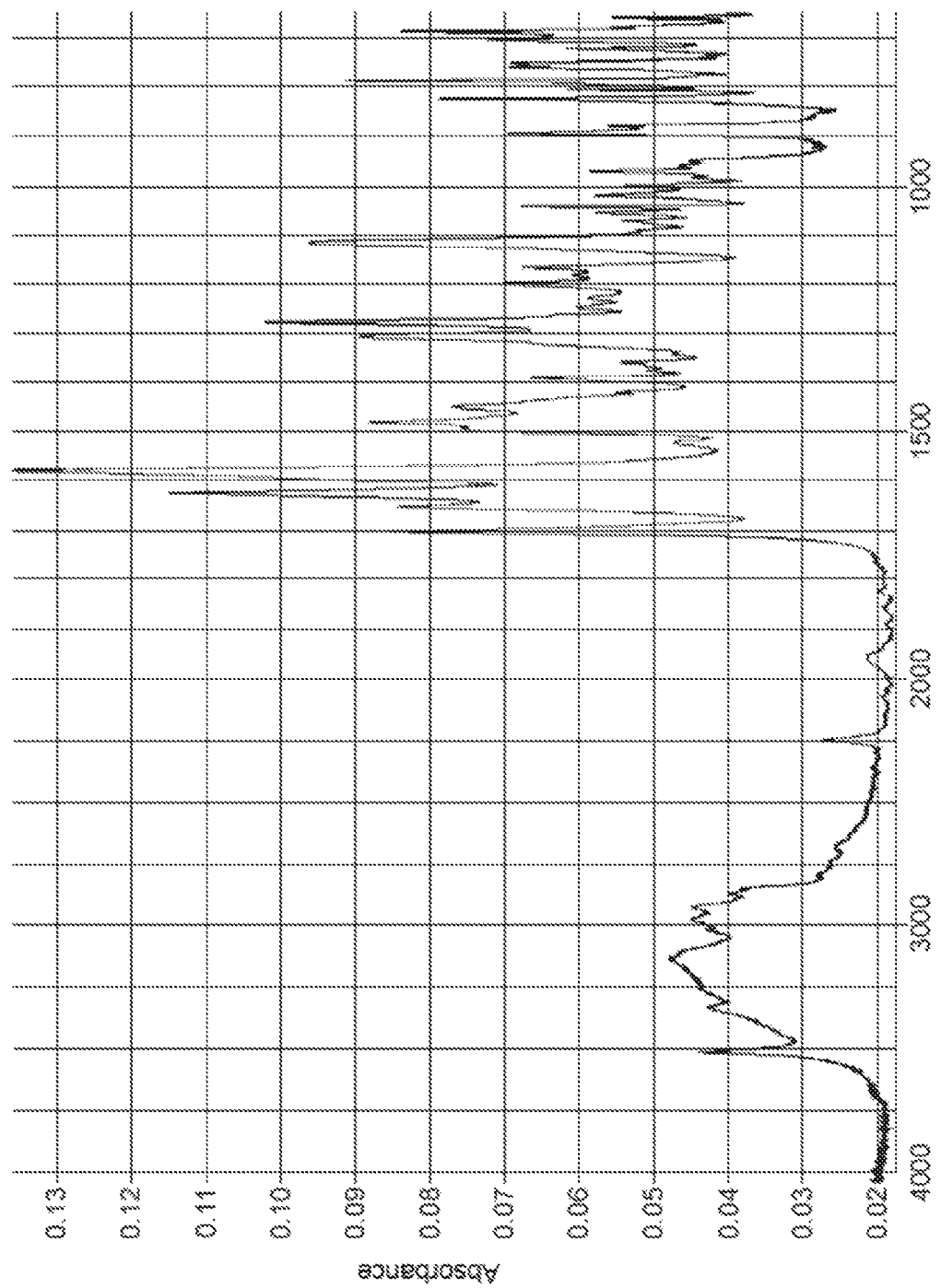
FIG. 8 shows an IR spectrum of a sample of compound of formula (I) in solid crystalline anhydrous form.

XRPD and IR:

The XPRD diffraction pattern of the reference sample is illustrated in FIG. 2 and the IR trace is illustrated in FIG. 8. This diffraction pattern and IR trace were compared with those of the comparative samples and the results are illustrated in Table 4. The diffraction patterns and IR traces were found to be identical for all samples, indicating that no solid state changes occurred after storage under different conditions.

Figure 10:
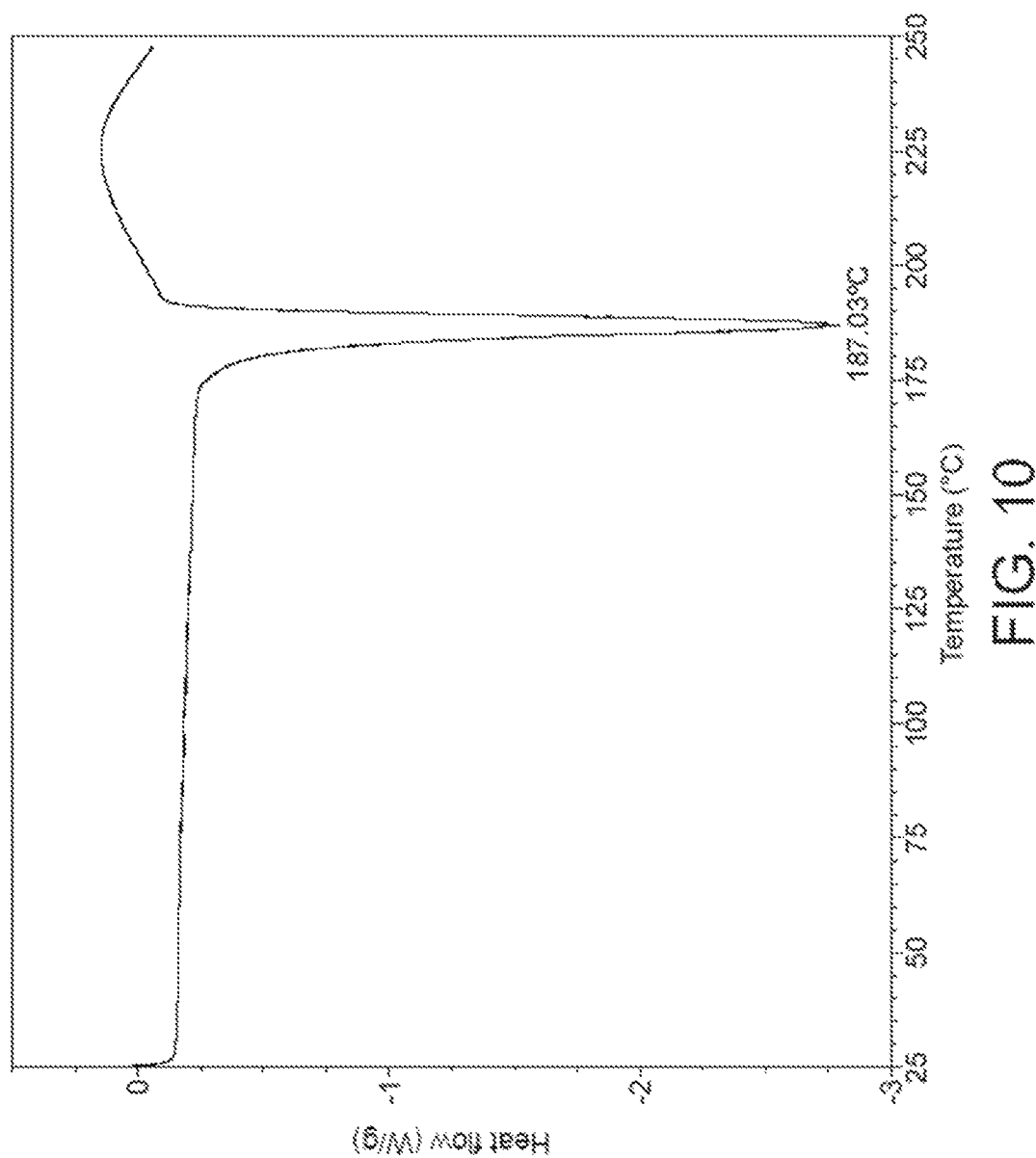
FIG. 10 shows thermal analysis of a sample of compound of formula (I) in solid crystalline anhydrous form by DSC.

DSC:

The reference sample and comparative samples were heated at 10° C./min from 25° C. to 250° C. The DSC curve of the reference sample is illustrated in FIG. 10 and the results for all samples are illustrated in Table 4. From FIG. 10, it is evident that the reference sample melted (with possible decomposition) at about 187.0° C. Comparing the DSC data of the reference sample with the data for the comparative samples it is evident that the storage conditions have not altered the melting point of the substance.

In summary, it is evident that the solid crystalline anhydrous form of compound of formula (I) was physically stable under all investigated conditions.

TABLE 4 stability data for the anhydrous form of the compound of formula (I) (unmicronized)

| Product | Condition | TGA <100 | TGA <200° C. | XRD | IR | DSC Max (° C.) | Appearance |
|---|---|---|---|---|---|---|---|
| Anhydrous Form (unmicronized) | 0 days | 0.2 | 0.4 | Cryst., Ref | Cryst., Ref | 187.0 | white |
| | 80° C. | — | — | ~Ref | ~Ref | — | white |
| | RT/<5% RH | 0.3 | 0.5 | ~Ref | ~Ref | 187.6 | white |
| | RT/56% RH | 0.4 | 0.5 | ~Ref | ~Ref | 187.4 | white |
| | RT/75% RH | 0.3 | 0.4 | ~Ref | ~Ref | 187.0 | white |
| | 50° C. | 0.3 | 0.4 | ~Ref | ~Ref | 187.2 | white |
| | 40° C./75% RH | 0.4 | 0.5 | ~Ref | ~Ref | 187.2 | white |

Solid Crystalline Anhydrous Form (Micronized)
TGA:

The reference sample and comparative samples were heated at 20° C./min from room temperature to 300° C. and the results for all samples are illustrated in Table 5.

Figure 13:
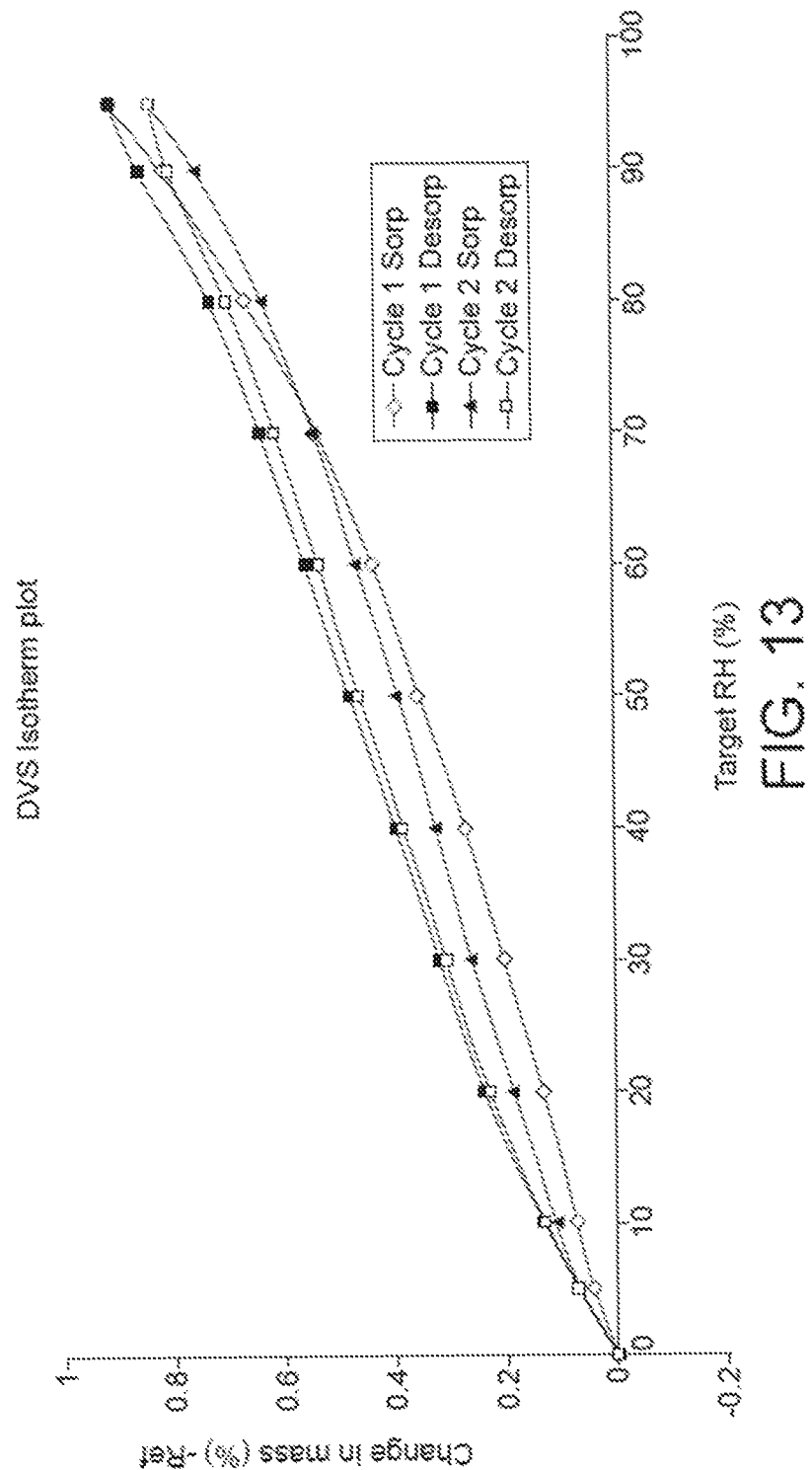
FIG. 13 shows a DVS isotherm plot of a sample of micronized compound of formula (I) in solid crystalline anhydrous form.

DVS:

The DVS isotherm plot for the reference sample is illustrated in FIG. 13. During the initial drying step, a weight loss of 0.1% was registered. The product was observed to be slightly hygroscopic, adsorbing up to 0.9% moisture depending on the atmospheric conditions. During the desorption cycle the product was found to dry out completely.

XRPD and IR:

The diffraction pattern and IR trace of the reference sample were compared with those of the comparative samples and the results are illustrated in Table 5. The diffraction patterns and IR traces were found to be identical for all samples, indicating that no solid state changes occurred after storage under different conditions.

DSC:

The reference sample and comparative samples were heated at 10° C./min from 25° C. to 250° C. The results for all samples are illustrated in Table 5. The DSC curve for the reference sample showed melting of the product (with possible decomposition) at about 186° C. An extra exothermic signal was observed at about 124° C. probably due to recrystallization of amorphous material or crystal artifacts present in the sample generated during milling.

In summary, it is evident that the solid crystalline anhydrous form of compound of formula (I) in micronized form was physically stable under all investigated conditions, although it is slightly hygroscopic.

relative humidities (comparative samples). The samples were stored under various conditions for 1, 4 or 8 weeks as shown in Tables 6, 7 and 8. The samples were then analyzed by HPLC using the method in General Procedures and by visual inspection.

Hydrate Form

From the data provided in Table 6 it is evident that the hydrate form of compound of formula (I) is chemically stable although some sensitivity to light was observed.

TABLE 5 stability data for the anhydrous form of the compound of formula (I) (micronized)

| | | TGA | | | | DSC | | |
| | | | | | | Max | Extra | |
| Product | Condition | <100 | <200° C. | XRD | IR | (° C.) | (° C.) | Appearance |
| Anhydrous Form (micronized) | 0 days | 0.2 | 0.4 | Cryst., Ref | Cryst., Ref | 185.6 | 123.4 (4 J/g) | white |
| | 80° C. | — | — | ~Ref | ~Ref | — | — | white |
| | RT/<5% RH | 0.3 | 0.4 | ~Ref | ~Ref | 185.7 | 123.7 (4 J/g) | white |
| | RT/56% RH | 0.4 | 0.4 | ~Ref | ~Ref | 185.5 | 123.0 (4 J/g) | white |
| | RT/75% RH | 0.3 | 0.4 | ~Ref | ~Ref | 185.6 | 123.3 (4 J/g) | white |
| | 50° C. | 0.5 | 0.4 | ~Ref | ~Ref | 185.4 | 124.9 (4 J/g) | white |
| | 40° C./75% RH | 0.2 | 0.3 | ~Ref | ~Ref | 185.7 | 124.5 (2 J/g) | white |

Example 5

HPLC Analysis of Compound of Formula (I) in Solid Crystalline Hydrate and Solid Crystalline Anhydrous Form (Anhydrous Form—Unmicronized and Micronized)

The chemical stability of the solid crystalline hydrate form and solid crystalline anhydrous form (anhydrous form both unmicronized and micronized) of the compound of formula (I) was determined by comparing a sample at ambient temperature and relative humidity (reference sample) with samples stored at various temperatures and

TABLE 6 stability data for the hydrate form of the compound of formula (I)

| | | HPLC Sum of impurities | | | Appearance | | |
| Product | Condition | 1 week | 4 weeks | 8 weeks | 1 week | 4 weeks | 8 weeks |
| Hydrate | Reference | 1.52 | — | — | white | — | — |
| | 0.3 days ICH light* | 1.61 | — | — | white | — | — |
| | 80° C. | 1.58 | — | — | white | — | — |
| | 40° C./75% RH | 1.54 | 1.46 | 1.54 | white | white | white |
| | 50° C. | 1.53 | 1.53 | 1.59 | white | white | white |
| | RT/<5% RH | — | 1.50 | 1.53 | — | white | white |
| | RT/56% RH | — | 1.53 | 1.54 | — | white | white |
| | RT/75% RH | — | 1.48 | 1.60 | — | white | white |

*stimulated daylight (light cabinet 700 W/m$^2$)

Anhydrous Form (Unmicronized)

From the data provided in Table 7 it is evident that the anhydrous form of compound of formula (I) is sensitive to light. After storage in ICH light for 0.3 days, a degradation product was observed at RRT 1.12 and RRT 1.24.

TABLE 7 stability data for the anhydrous form of the compound of formula (I) (solid state)

| Product | Condition | HPLC Sum of impurities | | | Appearance | | |
|---|---|---|---|---|---|---|---|
| | | 1 week | 4 weeks | 8 weeks | 1 week | 4 weeks | 8 weeks |
| Anhydrous Form (unmicronized) | Reference | 0.72 | — | — | white | — | — |
| | 0.3 da ICH light | 1.08 | — | — | slightly yellow | — | — |
| | 80° C. | 0.71 | — | — | white | — | — |
| | 40° C./75% RH | 0.71 | 0.72 | 0.72 | white | white | white |
| | 50° C. | 0.71 | 0.71 | 0.73 | white | white | white |
| | RT/<5% RH | — | 0.72 | 0.74 | — | white | white |
| | RT/56% RH | — | 0.71 | 0.77 | — | white | white |
| | RT/75% RH | — | 0.71 | 0.74 | — | white | white |

Anhydrous Form (Micronized)

From Table 8 it is evident that the anhydrous form of compound of formula (I) in micronized form is sensitive to light. After storage in ICH light for 0.3 days, a degradation product was observed at RRT 1.12.

TABLE 8 stability data for the anhydrous form of the compound of formula (I) (micronized)

| Product | Condition | HPLC Sum of impurities | | | Appearance | | |
|---|---|---|---|---|---|---|---|
| | | 1 week | 4 weeks | 8 weeks | 1 week | 4 weeks | 8 weeks |
| Anhydrous Form (micronized) | Reference | 0.72 | — | — | white | — | — |
| | 0.3 da ICH light | 0.89 | — | — | slightly yellow | — | — |
| | 80° C. | 0.71 | — | — | white | — | — |
| | 40° C./75% RH | 0.72 | 0.71 | 0.76 | white | white | white |
| | 50° C. | 0.71 | 0.71 | 0.76 | white | white | white |
| | RT/<5%RH | — | 0.70 | 0.73 | — | white | white |
| | RT/56%RH | — | 0.71 | 0.74 | — | white | white |
| | RT/75%RH | — | 0.73 | 0.75 | — | white | white |

The HPLC studies indicate that the chemical stabilities of the hydrate and anhydrous forms (both unmicronized and micronized) of compound of formula (I) are comparable, although all forms show some sensitivity to light.

Example 6

XRPD/IR Analysis of Compound of Formula (I) in Hydrate Form with Lactose, and in Anhydrous Form with Lactose Mixtures of the hydrate form of compound of formula (I) with lactose, and the anhydrous form (micronized) of compound of formula (I) with lactose (in each case 50%150%) were prepared, using LactoHale® as lactose source (supplied by DOMO®/Frieslandfoods). The mixtures were stored under different temperatures and humidities and were analysed by XRPD and IR at time zero and after 1 week and 4 weeks of storage. The IR spectra and the XRPD patterns of the 1 and 4 week stability samples were compared with the IR spectrum and XRPD pattern generated at time zero.

Solid Crystalline Hydrate

Blend preparation: about 250 mg of compound of formula (I) in hydrate form and 250 mg Lactohale200® were added to an agate mortar before being mixed using a pestle and plastic blade (Feton) for 5 minutes. The physical blends were filled in 10 mL brown glass flasks with screw lid (closed) and without lid (open). The following storage conditions were used:

80° C.: 1 week closed;
50° C.: 1 and 4 weeks closed;
40° C./75% RH: 1 and 4 weeks open.

Figure 14:
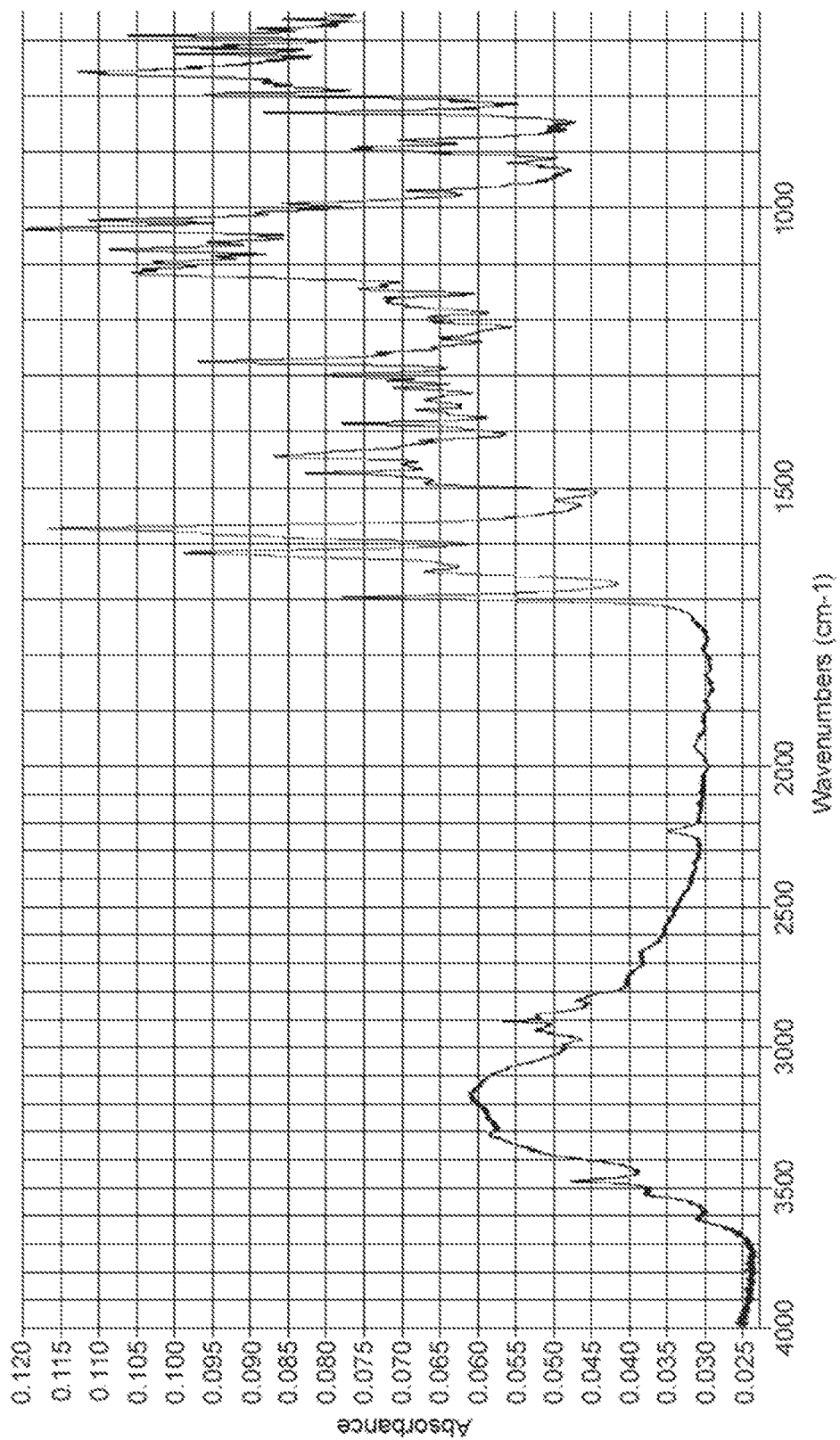
FIG. 14 shows an IR spectrum of a sample of a blend of compound of formula (I) in solid crystalline hydrate form and Lactohale200®.

A reference IR spectrum of a sample of a blend of solid crystalline hydrate form with lactose is shown in FIG. 14. IR spectra were acquired after the various storage conditions. No differences were observed between the IR spectra of the 1 and 4 week stability samples and the IR spectrum at time zero. No interaction between the hydrate form and lactose was observed and the hydrate form remained stable under all storage conditions.

Figure 15:
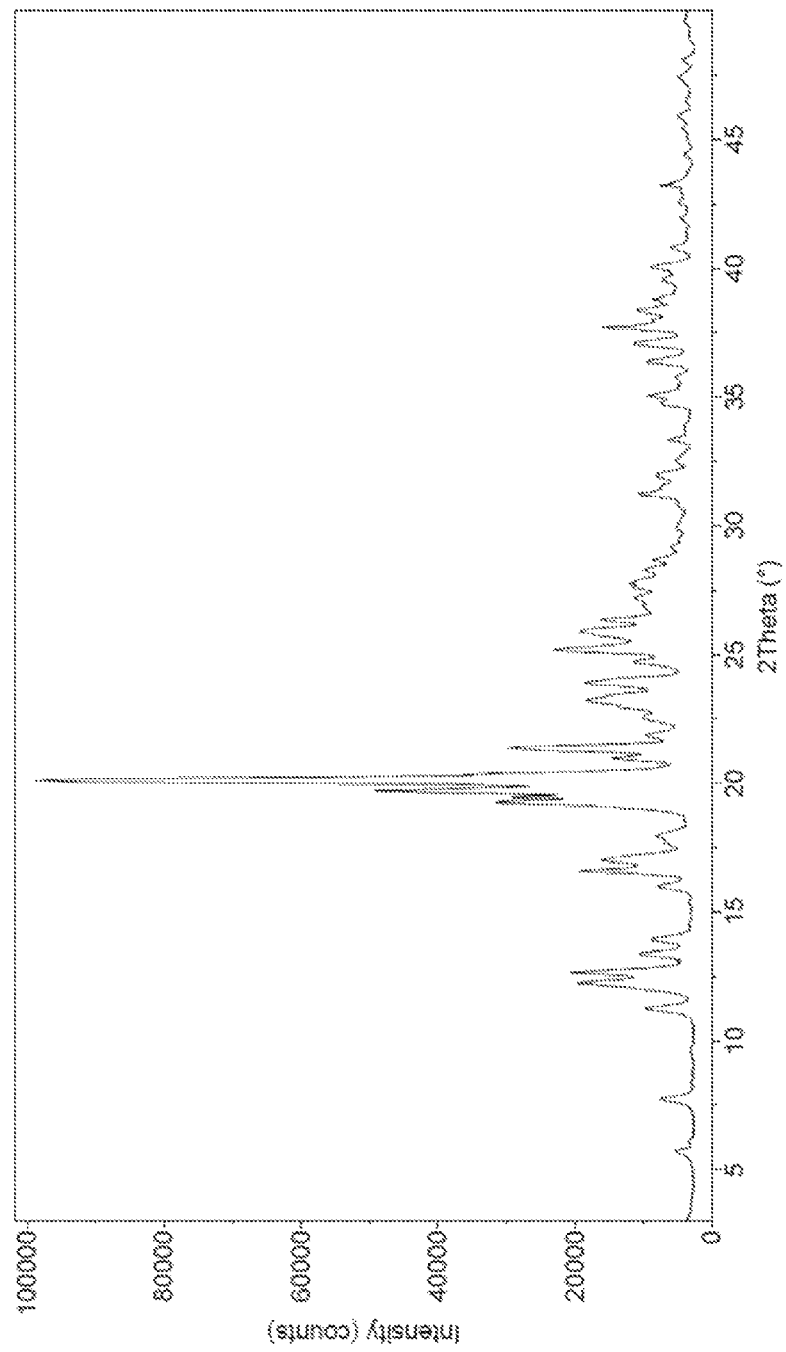
FIG. 15 shows an XRPD pattern acquired on a sample of a blend of compound of formula (I) in solid crystalline hydrate form and Lactohale200®.

A reference XRPD pattern of a sample of a blend of solid crystalline hydrate form with lactose is shown in FIG. 15. XRPD patterns were acquired after the various storage conditions. The generated XRPD patterns of the 1 and 4 week stability samples were similar to the diffraction pattern at time zero. It was clearly visible that the typical diffraction peaks of the hydrate form did not change in the presence of Lactohale200®, indicating that the hydrate form is physically stable in the presence of lactose.

The IR spectra showed no interaction between the hydrate form and the lactose, and the XRPD results showed that there was no solid state conversion of the hydrate form. As such, it may be concluded that the hydrate form is physically compatible with lactose.

Solid Crystalline Anhydrous Form

Blend preparation: about 500 mg of anhydrous compound of formula (I) (micronized) and 500 mg Lactohale200® were added to an agate mortar before being mixed using a pestle and plastic blade (Feton) for 5 minutes. The physical blends were filled in 10 mL brown glass flasks with screw lid (closed) and without lid (open). The following storage conditions were used:

80° C.: 1 week closed;
50° C.: 1 and 4 weeks closed;
40° C./75% RH: 1 and 4 weeks open.

Figure 16:
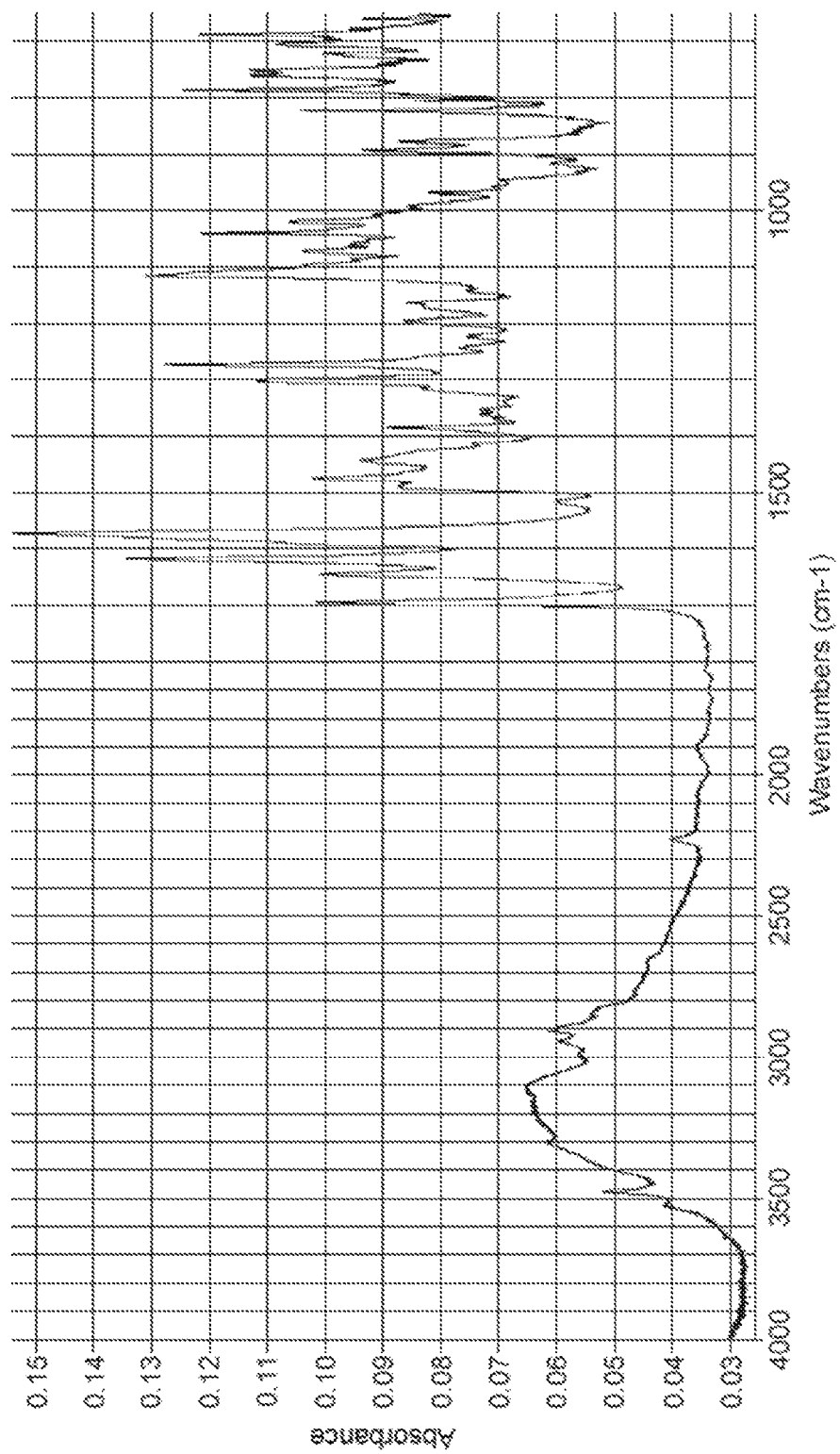
FIG. 16 shows an IR spectrum of a sample of a blend of compound of formula (I) in solid crystalline anhydrous (micronized) form and Lactohale200®.

A reference IR spectrum of a sample of a blend of solid crystalline anhydrous form (micronized) with lactose is shown in FIG. 16. IR spectra were acquired after the various storage conditions. No differences were observed between the IR spectra of the 1 and 4 week stability samples and the IR spectrum at time zero. No interaction between the anhydrous form and lactose was observed and the anhydrous form remained stable under all storage conditions.

Figure 17:
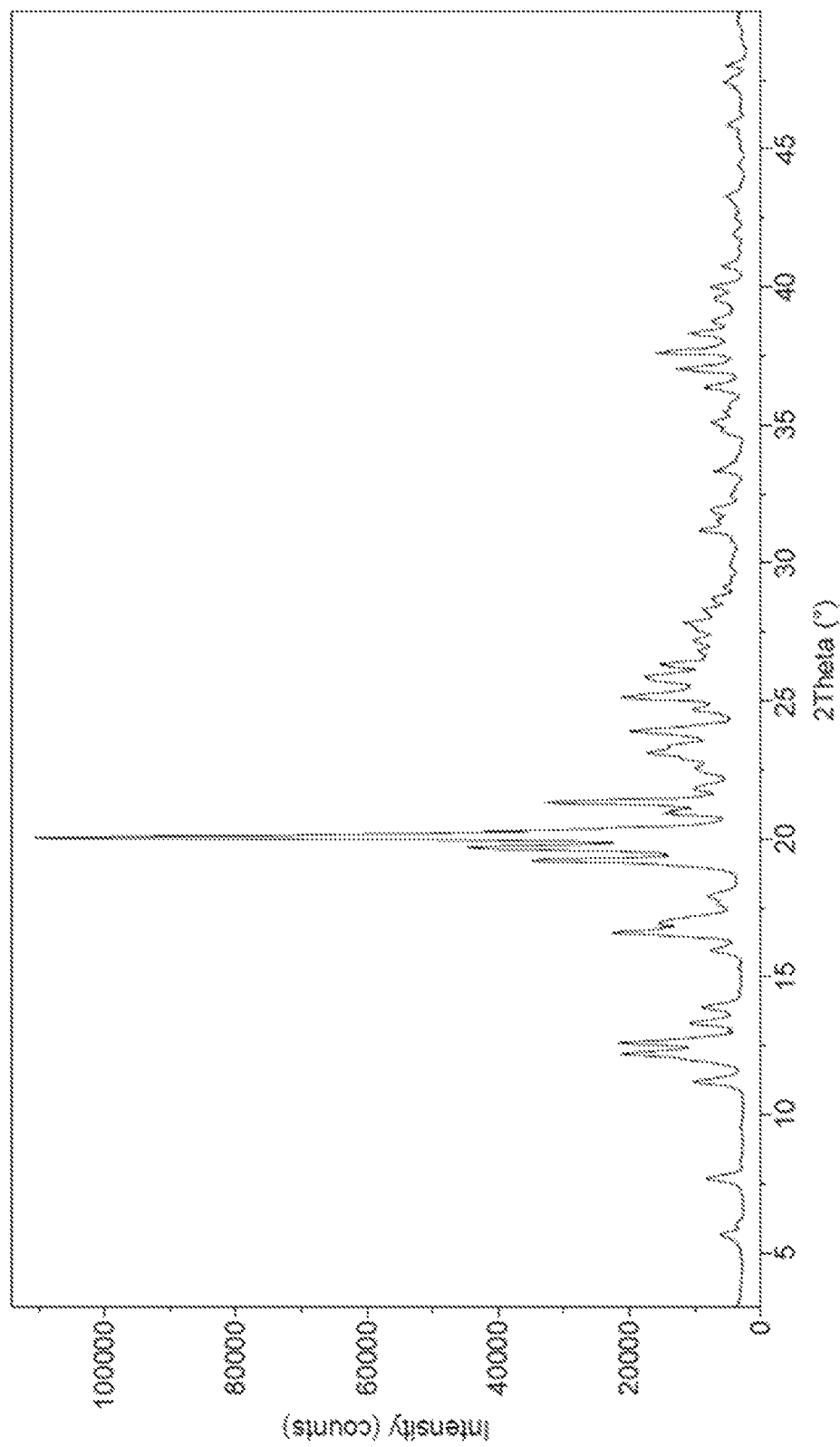
FIG. 17 shows an XRPD pattern acquired on a sample of a blend of compound of formula (I) in solid crystalline anhydrous form (micronized) and Lactohale200®.

A reference XRPD patterns of a sample of a blend of solid crystalline anhydrous form (micronized) with lactose is shown in FIG. 17. XRPD patterns were acquired after the various storage conditions. The generated XRPD patterns of the 1 and 4 week stability samples are similar to the diffraction pattern at time zero. It is clearly visible that the typical diffraction peaks of the anhydrous form did not change in the presence of Lactohale200®, indicating that the anhydrous form is physically stable in the presence of lactose.

The IR spectra showed no interaction between the anhydrous form and the lactose, and the XRPD results showed that there was no solid state conversion of the anhydrous form. As such, it may be concluded that the anhydrous form is physically compatible with lactose.

Example 7

HPLC Analysis of Compound of Formula (I) in Solid Crystalline Hydrate Form with Lactose, and in Solid Crystalline Anhydrous Form with Lactose The chemical compatibility of the hydrate form and anhydrous form of compound of formula (I) in combination with lactose was determined by HPLC analysis.

Hydrate

Blend preparation: 2 mg of hydrate form and 2 mg of Lactohale200® were added to an agate mortar before being mixed using a pestle and plastic blade (Feton) for 5 minutes. Further aliquots of Lactohale200® (starting at 4 mg) were mixed into the blend, doubling the volume of the mixture each time, until the mixture contained 6000 mg Lactohale200® in total.

The mixtures were analysed by HPLC at time zero and after different conditions of storage. Samples were stored under the following conditions: (i) 1, 2 and 3 weeks at 50° C. (ii) 1 week 80° C. (iii) 1, 2 and 3 weeks at 40° C./75% RH. From Table 9 it is evident that the hydrate form of compound of formula (I) is stable in combination with lactose for up to 3 weeks, indicating their chemical compatibility.

TABLE 9 stability data for the hydrate form of the compound of formula (I) with lactose

| Conditions | RRT* 0.80 | RRT* 0.84 | RRT* 0.86 | RRT* 1.11 | RRT* 1.14 | RRT* 1.32 |
|---|---|---|---|---|---|---|
| T = zero | 0.15 | 0.13 | 0.15 | 0.09 | 0.15 | 0.92 |
| 1 week 50° C. | 0.14 |  | 0.31 |  | 0.15 | 0.94 |
| 1 week 80° C. |  | 0.15 |  | 0.12 | 0.15 | 0.91 |
| 1 week 40° C./75% RH | 0.16 | 0.13 | 0.18 |  | 0.24 | 0.93 |
| 2 weeks 50° C. | 0.15 | 0.13 | 0.12 | 0.10 | 0.16 | 0.91 |
| 2 weeks 40° C. 75% RH | 0.13 | 0.13 | 0.15 | 0.10 | 0.17 | 0.92 |
| 3 weeks 50° C. | 0.14 | 0.11 | 0.17 | 0.08 | 0.14 | 0.99 |
| 3 weeks 40° C. 75% RH | 0.14 | 0.10 | 0.13 | 0.08 | 0.14 | 1.00 |

*Area % by HPLC at RRT indicated. Compound of formula (I) has RRT = 1.0

Anhydrous (Micronized)

Micronized anhydrous form of compound of formula (I) was prepared as described in Example 4.

The test batch was taken from stock containing 3.519 mg anhydrous form of compound of formula (I) (micronized) and 6006.64 mg Lactohale200®.

The mixtures were analysed by HPLC at time zero and after different conditions of storage. Samples were stored under the following conditions: (i) 1, 2, 3 and 4 weeks at 50° C. (ii) 1 week 80° C. (iii) 1, 2, 3 and 4 weeks at 40° C./75% RH.

Table 10 indicates that significant degradation was observed after storage for 1 week at 80° C. and degradation was also observed after storage at elevated temperatures of 50° C. These results suggest that the anhydrous form (micronized) of compound of formula (I) is not chemically stable in combination with lactose, therefore the two components would not be compatible in a pharmaceutical formulation.

The peak at RRT 0.86 has been attributed to the hydrated derivative(s) D019328 shown above.

TABLE 10 stability data for the solid crystalline anhydrous form of the compound of formula (I) (micronized) with lactose

| Conditions | RRT* 0.80 | RRT* 0.86 | RRT* 0.97 | RRT* 1.14 | RRT* 1.32 |
|---|---|---|---|---|---|
| T = zero | 0.21 | 0.12 | 0.78 | 0.12 | 0.13 |
| 1 week 50° C. | 0.17 | 0.23 |  | 0.10 | 0.12 |
| 1 week 80° C. | 0.52 | 2.53 |  | 0.19 | 0.12 |
| 1 week 40° C./75% RH | 0.19 | 0.12 |  | 0.11 | 0.13 |
| 2 weeks 50° C. | 0.19 | 0.30 |  | 0.12 | 0.13 |
| 2 weeks 40° C./75% RH | 0.17 | 0.11 |  | 0.12 | 0.13 |
| 3 weeks 50° C. | 0.19 | 0.38 |  | 0.12 | 0.14 |
| 3 weeks 40° C./75% RH | 0.19 | 0.08 |  | 0.11 | 0.14 |
| 4 w 50° C. | 0.19 | 0.54 |  | 0.11 | 0.13 |
| 4 w 40° C./75% RH | 0.18 | 0.20 |  | 0.11 | 0.14 |

*Area % by HPLC at RRT indicated.
Compound of formula (I) has RRT = 1.0

Example 8

XRPD/IR Analysis of Compound of Formula (I) in Solid Crystalline Anhydrous Form with Lactose and Magnesium Stearate A mixture of the solid crystalline anhydrous form (micronized) of compound of formula (I) with lactose was prepared with the addition of 1% magnesium stearate. The mixtures were stored under different temperatures and humidities and were analysed by XRPD and IR at time zero and after 1 week and 4 weeks of storage.

Blend preparation: about 500 mg of Lactohale200 and about 10 mg magnesium stearate were added to an agate mortar before being mixed using a pestle and plastic blade (Feton) for 5 minutes. About 500 mg of anhydrous compound of formula (I) (micronized) was added to the mixture and the blend was mixed for a further 5 minutes. Samples of the blend were then stored under the various conditions described in Example 6.

Figure 18:
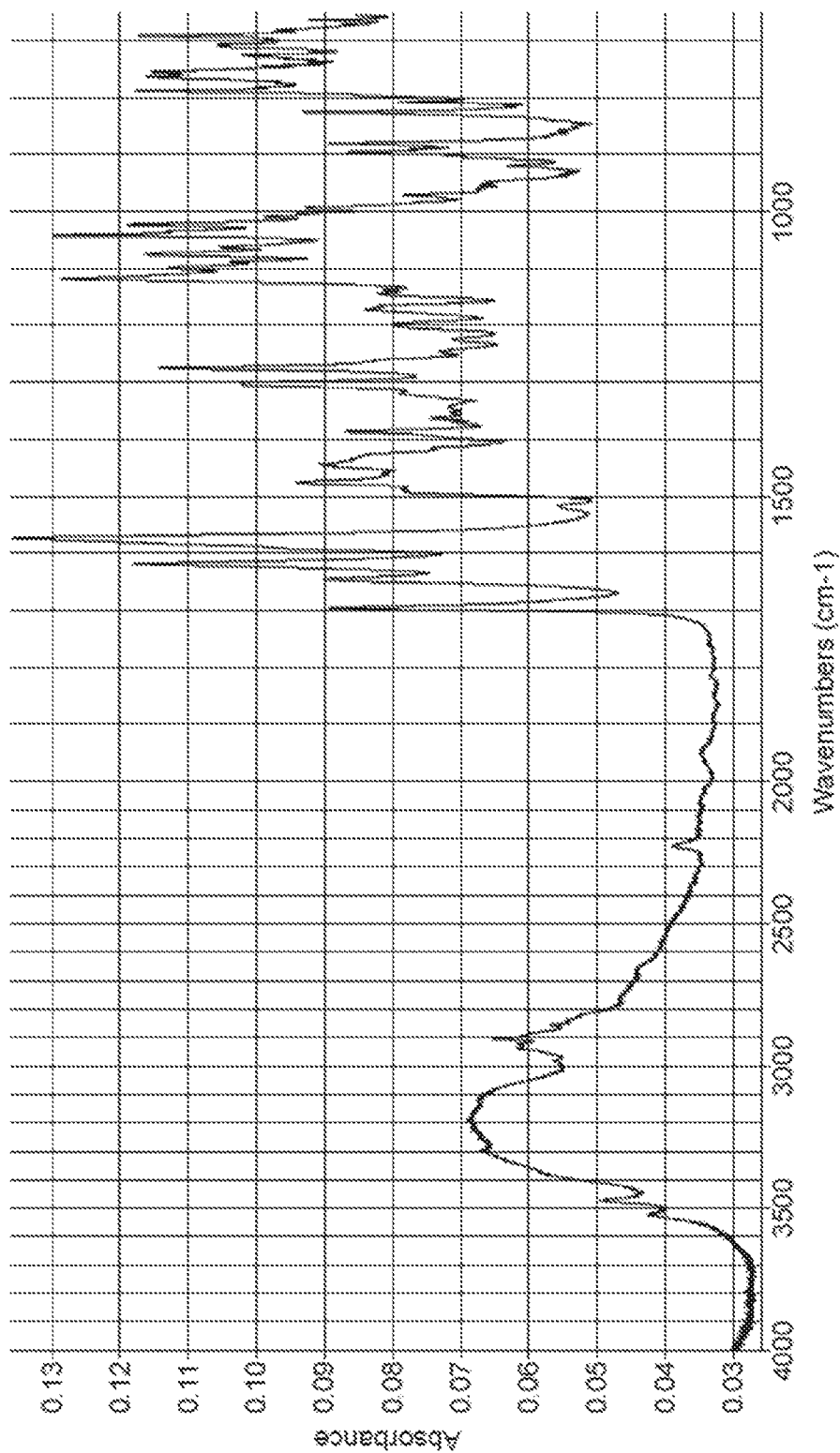
FIG. 18 shows an IR spectrum of a sample of a blend of compound of formula (I) in solid crystalline anhydrous form (micronized), Lactohale200® and magnesium stearate.

A reference IR spectrum of a sample of a blend of solid crystalline anhydrous form (micronized) with lactose and magnesium stearate is shown in FIG. 18. IR spectra were acquired after the various storage conditions. No differences were observed between the IR spectra of the 1 and 4 week stability samples and the IR spectrum at time zero. No interaction between the anhydrous form; lactose and magnesium stearate was observed and the anhydrous form remained stable under all storage conditions.

Figure 19:
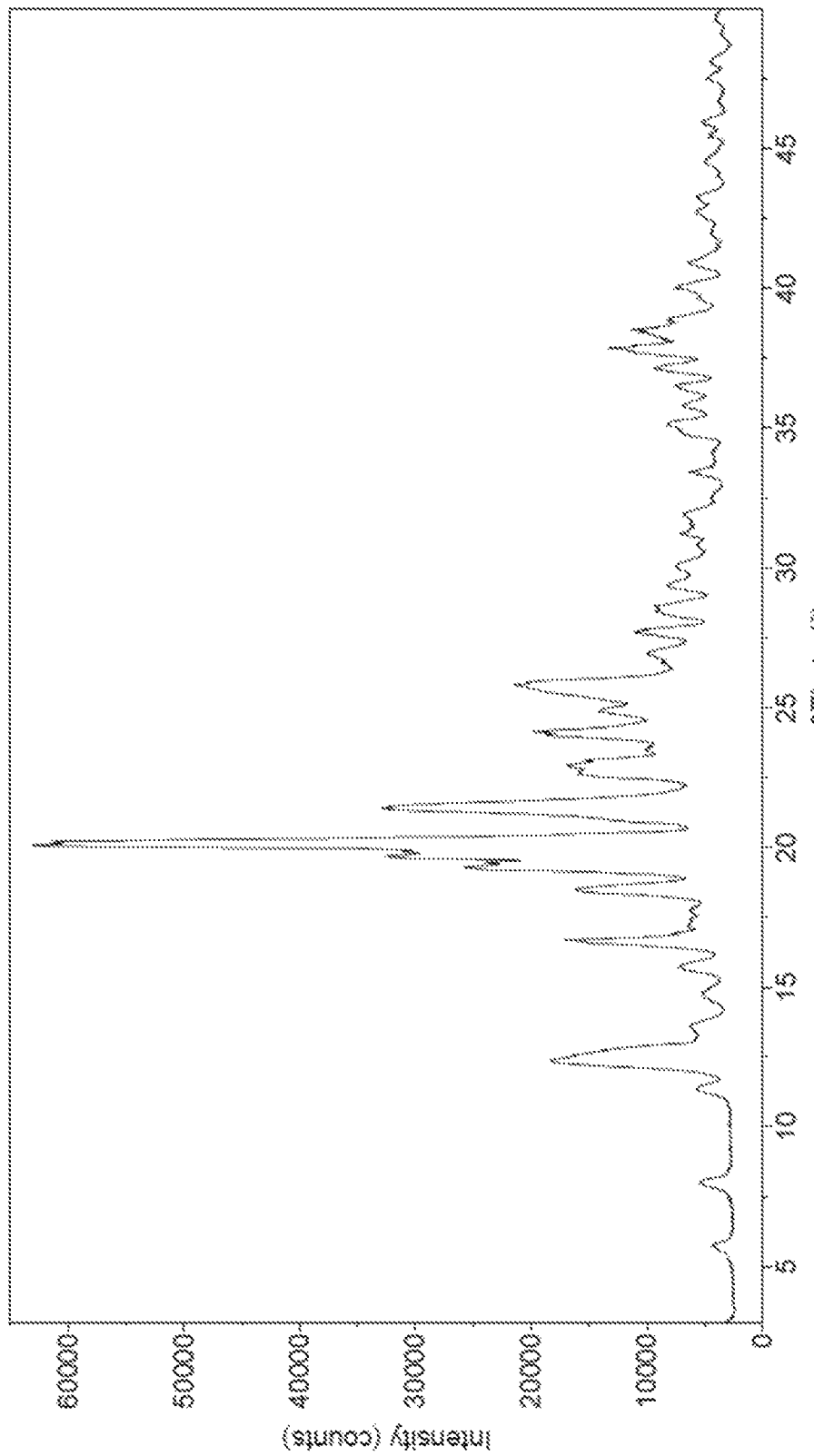
FIG. 19 shows an XRPD pattern acquired on a sample of a blend of compound of formula (I) in solid crystalline anhydrous form (micronized), Lactohale200® and magnesium stearate

A reference XRPD pattern of a sample of a blend of solid crystalline anhydrous form (micronized) with lactose and magnesium stearate is shown in FIG. 19. XRPD patterns were acquired after the various storage conditions. The generated XRPD patterns of the 1 and 4 week stability samples were similar to the diffraction pattern at time zero. It was clearly visible that the typical diffraction peaks of the anhydrous form did not change in the presence of Lactohale200® and magnesium stearate, indicating that the anhydrous form is physically stable in the presence of lactose and magnesium stearate.

The IR spectra showed no interaction between the anhydrous form, the lactose and the magnesium stearate, and the XRPD results showed that there was no solid state conversion of the anhydrous form. As such, it may be concluded that the anhydrous form is physically compatible with lactose and magnesium stearate.

Example 9

HPLC Analysis of Compound of Formula (I) in Anhydrous Form with Lactose and Magnesium Stearate The chemical compatibility of the solid crystalline anhydrous form of compound of formula (I) in combination with lactose and 1% magnesium stearate was determined by HPLC analysis.

The test batch was taken from stock containing 3.704 mg anhydrous form of compound of formula (I) (micronized), 6017.90 mg Lactohale200 and 67.33 mg magnesium stearate.

The data shown in Table 11 indicate a significant increase in chemical stability compared with the same composition with the absence of magnesium stearate (see Table 2), as evidenced by only a small amount of degradation observed after storage for 1 week at 80° C. (see e.g. RRT 0.86, 0.28%). These results suggest that the chemical stability of the anhydrous form (micronized) of compound of formula (I) with lactose is significantly improved by the addition of magnesium stearate to the composition. As such, the addition of magnesium stearate improves the chemical compatibility of the anhydrous form (micronized) of compound of formula (I) in combination with lactose such that they could be compatible in a pharmaceutical formulation.

TABLE 11 stability data for the anhydrous form of the compound of formula (I) (micronized) with lactose and magnesium stearate

| Conditions | RRT* 0.80 | RRT* 0.86 | RRT* 1.14 | RRT* 1.32 |
|---|---|---|---|---|
| T = zero | 0.21 | 0.10 | 0.12 | 0.13 |
| 1 week 50° C. | 0.20 | 0.11 | 0.11 | 0.13 |
| 1 week 80° C. | 0.19 | 0.28 | 0.11 | 0.13 |
| 1 week 40° C./75% RH | 0.20 | 0.11 | 0.11 | 0.13 |
| 2 weeks 50° C. | 0.20 | 0.08 | 0.11 | 0.14 |
| 2 weeks 40° C./75% RH | 0.21 | 0.11 | 0.11 | 0.13 |
| 3 weeks 50° C. | 0.20 | 0.13 | 0.11 | 0.13 |
| 3 weeks 40° C./75% RH | 0.20 | 0.11 | 0.11 | 0.14 |
| 4 weeks 50° C. | 0.19 | 0.12 | 0.11 | 0.14 |
| 4 weeks 40° C./75% RH | 0.20 | 0.10 | 0.10 | 0.13 |

*Area % by UPLC at RRT indicated.
Compound of formula (I) has RRT = 1.0

Example 10

UPLC Analysis of Compound of Formula (I) in Anhydrous Form with Lactose and Metal Salts of Stearic Acid The chemical compatibility of the solid crystalline anhydrous form of compound of formula (I) (micronized) in combination with lactose and 1% metal salt of stearic acid (magnesium stearate, sodium stearate and calcium stearate) was determined by UPLC analysis (micronization of compound of formula (I) as described in Example 4).

Test samples were prepared as described in Table 12 below:

TABLE 12 test samples for UPLC analysis after accelerated stability testing

| Sample | solid crystalline anhydrous form of compound of formula (I) (micronized) sample 1/sample 2 | Lactohale 200 sample 1/sample 2 | Metal salt of stearic acid sample 1/sample 2 |
|---|---|---|---|
| Drug only | 0.50 mg/0.47 mg | | |
| Drug and lactose | 0.58 mg/0.47 mg | 749.84 mg/750.06 mg | |
| Drug, lactose, Mg stearate | 0.46 mg/0.51 mg | 749.97 mg/751.59 mg | 7.40 mg/7.55 mg |

TABLE 12-continued test samples for UPLC analysis after accelerated stability testing

| Sample | solid crystalline anhydrous form of compound of formula (I) (micronized) sample 1/sample 2 | Lactohale 200 sample 1/ sample 2 | Metal salt of stearic acid sample 1/ sample 2 |
|---|---|---|---|
| Drug, lactose, Ca stearate | 0.49 mg/0.45 mg | 751.08 mg/ 753.53 mg | 7.67 mg/ 7.80 mg |
| Drug, lactose, Na stearate | 0.48 mg/0.45 mg | 750.20 mg/ 750.42 mg | 7.78 mg/ 7.59 mg |

Samples were dispensed into vials, sealed with caps and kept at 80° C. for 1 or 2 weeks.

Sample 1 was used for the 1 week studies and sample 2 was used for the 2 week studies.

Results are shown in Table 13 below:

TABLE 13 results of UPLC analysis after accelerated stability testing

| Sample | 1 week 80° C. RRT* 0.87 | 1 week 80° C. RRT* 0.92 | 2 weeks 80° C. RRT* 0.87 | 2 weeks 80° C. RRT* 0.92 |
|---|---|---|---|---|
| Drug only | 0.00 | 0.08 | 0.00 | 0.08 |
| Drug and lactose | 0.58 | 0.39 | 1.80 | 0.77 |
| Drug, lactose, Mg stearate | 0.28 | 0.29 | 0.06 | 0.18 |
| Drug, lactose, Ca stearate | 0.11 | 0.19 | 0.17 | 0.19 |
| Drug, lactose, Na stearate | 0.00 | 0.09 | 0.00 | 0.09 |

*Area % by UPLC at RRT indicated.
Compound of formula (I) has RRT = 1.0

Mass spectroscopy analysis indicates that the substance with RRT 0.87 is D019493 and the substance with RRT 0.92 is D019492 (confirmed by NMR) (see Scheme 1). The NMR resonance assignments for D019492 are given in Table 14:

TABLE 14

$^1$H NMR resonance assignments for D019492

| | $^1$H NMR assignments (600 MHz, DMSO-$d_6$) δ ppm |
|---|---|
| D019492 | 1.59 (quin, J = 7.30 Hz, 2 H) 2.20 (t, J = 7.55 Hz, 2 H) 2.46-2.49 (m, 2 H) 3.18 (d, J = 7.90 Hz, 6 H) 3.29-3.39 (m, 8 H) 4.23 (s, 2 H) 5.24 (s, 2 H) 5.76 (s, 2 H) 6.08 (d, J = 7.55 Hz, 1 H) 6.75 (t, J = 7.55 Hz, 1 H) 6.83 (dd, J = 8.12, 1.70 Hz, 1 H) 6.90 (d, J = 7.55 Hz, 1 H) 6.91-6.93 (m, 1 H) 7.01 (t, J = 7.55 Hz, 1 H) 7.09 (d, J = 7.55 Hz, 1 H) 7.29 (m, J = 7.93, 7.93 Hz, 1 H) 7.32 (d, J = 7.18 Hz, 1 H) 7.66 (d, J = 7.93 Hz, 1 H) 7.77-7.82 (m, 1 H) 8.17 (s, 1 H) 9.67 (s, 1H) |

The data shown in Table 13 indicate a significant increase in chemical stability for formulations containing a metal salt of stearic acid compared with the same composition in the absence of a metal salt of stearic acid, as evidenced by a comparatively small amount of degradation observed after storage for 1 or 2 weeks at 80° C. These results suggest that the chemical stability of the anhydrous form of compound of formula (I) with lactose is significantly improved by the addition of metal salts of stearic acid to the composition. Therefore the addition of metal salts of stearic acid improves the chemical compatibility of the anhydrous form of compound of formula (I) in combination with lactose such that they could be compatible in a pharmaceutical formulation.

Example 11

Preparation of Pharmaceutical Formulations According to the Invention

An exemplary pharmaceutical formulation of the invention consists of 0.5 wt. % of compound of formula (I) (solid crystalline anhydrous form, micronised), 98.5 wt. % lactose monohydrate (inhalation grade) and 1.0 wt. % magnesium stearate, wherein the wt. % of all components is based on the weight of the dry pharmaceutical formulation.

Summary of the Results Disclosed in the Examples

Solid crystalline anhydrous and hydrate forms of compound of formula (I) have been identified.

From the TGA, DVS, XRPD, IR and DSC studies, it is evident that the solid crystalline anhydrous form of compound of formula (I) (in both unmicronized and micronized forms) and the solid crystalline hydrate form are both stable, although the hydrate form has a tendency to lose some water under dry conditions, apparently without impact on its crystalline structure. The chemical stabilities of the hydrate and anhydrous forms of the compound of formula (I) are comparable.

When the solid crystalline hydrate and anhydrous forms were tested for their chemical compatibility with lactose, although both forms were found to be physically compatible, chemical degradation was observed for the solid crystalline anhydrous form in the presence of lactose.

However, the addition of magnesium stearate, calcium stearate or sodium stearate (examples of a metal salt of stearic acid) to the combination of the solid crystalline anhydrous form of compound of formula (I) and lactose was surprisingly found to significantly reduce chemical degradation. As such, a pharmaceutical formulation comprising compound of formula (I) in solid crystalline anhydrous form, lactose and a metal salt of stearic acid such as magnesium stearate has good physical and chemical stability.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A crystalline form of a compound of formula (I)

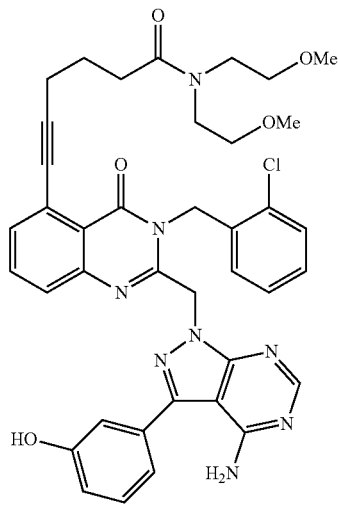

wherein the crystalline form is a hydrate or is anhydrous.

2. The crystalline form of claim 1, having an X-ray powder diffraction pattern comprising one, two, three or four peaks selected from peaks at 17.6°, 18.4°, 22.5° and 24.2° 2θ±0.2°.

3. The crystalline form of claim 1, wherein the crystalline form is a hydrate.

4. The crystalline form of claim 3, having an X-ray powder diffraction pattern comprising one, two, three, four, five, six or seven peaks selected from peaks at (±0.2) 9.6, 13.3, 13.9, 17.0, 18.9, 20.3, and 23.1 2 θ±0.2°.

5. The crystalline form of claim 1, wherein the crystalline form is anhydrous.

6. The crystalline form of claim 5, having an X-ray powder diffraction pattern comprising one, two, three, four, five, six or seven peaks selected from peaks at (±0.2°) 5.6, 7.9, 11.2, 12.3, 15.6, 17.6, 18.4, 21.4, and 24.2 ° 2θ(±0.2°).

7. A pharmaceutical composition comprising the crystalline form of claim 1 in admixture with one or more pharmaceutically acceptable diluents or carriers.

8. The pharmaceutical composition of claim 7, further comprising a stabilizing agent selected from the group consisting of metal salts of stearic acid and metal salts of stearyl fumarate.

9. The pharmaceutical composition of claim 8, wherein the stabilizing agent is magnesium stearate.

10. The pharmaceutical composition of claim 7, wherein the pharmaceutically acceptable diluent or carrier comprises lactose.

11. The pharmaceutical composition of claim 7, wherein the crystalline form is micronized.

12. An inhalation device comprising one or more doses of the pharmaceutical composition of claim 7.

13. A method of inhibiting phosphoinositide-3 kinase activity in a subject comprising administering to the subject an effective amount of the crystalline form of claim 1 or the pharmaceutical composition of claim 7.

14. A process for the preparation of the crystalline form of claim 3 comprising the step of crystallizing a compound of formula (I) from dichloromethane optionally in mixture with methanol.

15. A process for the preparation of the crystalline form of claim 5 comprising the step of crystallizing a compound of formula (I) from anhydrous 1-propanol.

16. The process of claim 15, wherein the crystallization step comprises cooling from an elevated temperature.

17. A crystalline form of a compound of formula (I)

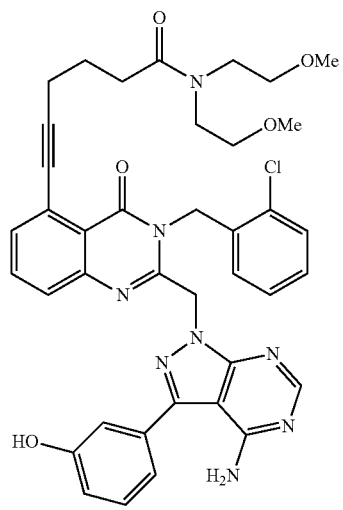

having the X-ray powder diffraction pattern as shown in FIG. 1.

18. A crystalline form of a compound of formula (I)

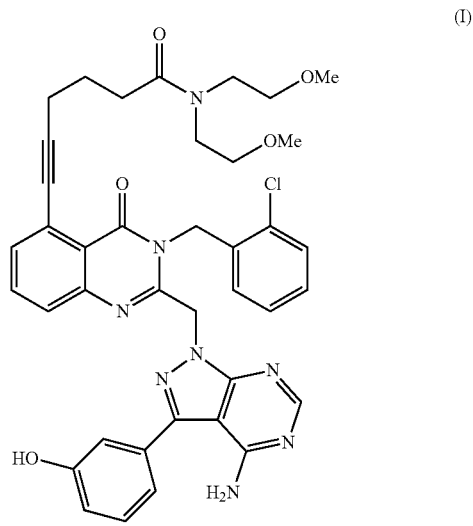 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

having the X-ray powder diffraction pattern as shown in FIG. 2.

* * * * *

UNITED STATES PATENT AND TRADEMARK OFFICE
CERTIFICATE OF CORRECTION

PATENT NO. : 9,642,799 B2  
APPLICATION NO. : 14/381289  
DATED : May 9, 2017  
INVENTOR(S) : Rudy Laurent Maria Broeckx et al.

Page 1 of 1

It is certified that error appears in the above-identified patent and that said Letters Patent is hereby corrected as shown below:

In the Claims

Column 41, Line 38, Claim 4, after "peaks selected from peaks at" delete "(± 0.2)".

Column 41, Line 39, Claim 4, after "and 23.1" delete "2 θ" and replace with -- 2θ --.

Column 41, Line 44, Claim 6, after "peaks selected from peaks at" delete "(± 0.2)".

Signed and Sealed this  
Twenty-eighth Day of May, 2019

Andrei Iancu  
*Director of the United States Patent and Trademark Office*